(12) United States Patent
Dar et al.

(10) Patent No.: US 9,433,774 B2
(45) Date of Patent: Sep. 6, 2016

(54) HEADSET FOR TREATMENT AND ASSESSMENT OF MEDICAL CONDITIONS

(71) Applicant: NEUROLIEF LTD., Yokneam Illit (IL)

(72) Inventors: Amit Dar, Kfar Hess (IL); Jonathan Bar-Or, Pardes Hana Karkur (IL); Amir Cohen, Ra'anana (IL); Ron Belson, Tel Aviv (IL)

(73) Assignee: NEUROLIEF LTD., Yokneam Illit (IL)

( * ) Notice: Subject to any disclaimer, the term of this patent is extended or adjusted under 35 U.S.C. 154(b) by 0 days.

(21) Appl. No.: 14/849,868

(22) Filed: Sep. 10, 2015

(65) Prior Publication Data

US 2015/0374971 A1    Dec. 31, 2015

Related U.S. Application Data

(63) Continuation-in-part of application No. PCT/IB2014/059858, filed on Mar. 15, 2014.

(60) Provisional application No. 61/786,701, filed on Mar. 15, 2013.

(51) Int. Cl.
| | |
|---|---|
| *A61N 1/00* | (2006.01) |
| *A61N 1/04* | (2006.01) |
| *A61N 1/36* | (2006.01) |
| *A61B 5/0478* | (2006.01) |
| *A61B 5/00* | (2006.01) |

(52) U.S. Cl.
CPC ........... *A61N 1/0484* (2013.01); *A61N 1/0476* (2013.01); *A61N 1/0488* (2013.01); *A61N 1/0492* (2013.01); *A61N 1/36014* (2013.01); *A61B 5/0478* (2013.01); *A61B 5/6803* (2013.01)

(58) Field of Classification Search
CPC ............. A61N 1/0484; A61N 1/0472; A61N 1/0476; A61N 1/0492; A61N 1/36014; A61N 1/0456; A61B 5/6803; A61B 5/6802; A61B 5/6814; A61B 5/683; A61B 5/6831; A61B 5/0478; A41F 1/008
See application file for complete search history.

(56) References Cited

U.S. PATENT DOCUMENTS

| | | | |
|---|---|---|---|
| 3,659,614 A | 5/1972 | Jankelson | |
| 5,495,853 A | 3/1996 | Yasushi | |
| 6,077,237 A * | 6/2000 | Campbell | ............... G06F 3/011 600/587 |
| 2001/0039444 A1 | 11/2001 | Bar-Or et al. | |
| 2007/0093706 A1 * | 4/2007 | Gevins | ................. A61B 5/0478 600/383 |
| 2010/0324441 A1 * | 12/2010 | Hargrove | ........... A61B 5/04004 600/544 |
| 2011/0301486 A1 * | 12/2011 | Van Hek | .............. A61B 5/6814 600/544 |
| 2011/0319975 A1 * | 12/2011 | Ho | ........................ A61N 1/0408 607/139 |
| 2013/0079659 A1 * | 3/2013 | Akhadov | ............. A61B 5/0476 600/544 |

(Continued)

FOREIGN PATENT DOCUMENTS

| | | |
|---|---|---|
| WO | WO9743954 A1 | 11/1997 |
| WO | WO2012079778 A1 | 6/2012 |
| WO | WO2013001526 A2 | 1/2013 |

OTHER PUBLICATIONS

International Search Report for PCT/IB2014/059858 dated Jul. 22, 2014.

(Continued)

*Primary Examiner* — Robert N Wieland
(74) *Attorney, Agent, or Firm* — Marc Van Dyke; Fourth Dimension IP

(57) ABSTRACT

A circumferential headset for use in delivering electrical stimulation to the skin surface of the head.

46 Claims, 15 Drawing Sheets

(56) References Cited

U.S. PATENT DOCUMENTS

| | | | |
|---|---|---|---|
| 2013/0204315 A1* | 8/2013 | Wongsarnpigoon | A61N 1/36021 607/45 |
| 2014/0200432 A1* | 7/2014 | Banerji | A61B 5/0488 600/383 |
| 2014/0213874 A1* | 7/2014 | Tong | A61B 5/6803 600/383 |

OTHER PUBLICATIONS

Written Opinion for PCT/IB2014/059858 dated Jul. 22, 2014.

* cited by examiner

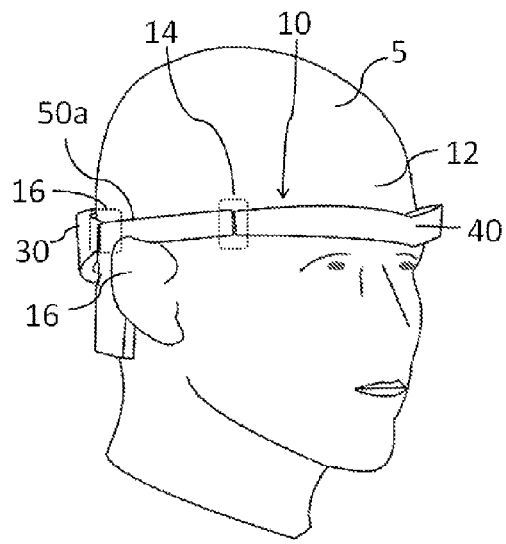
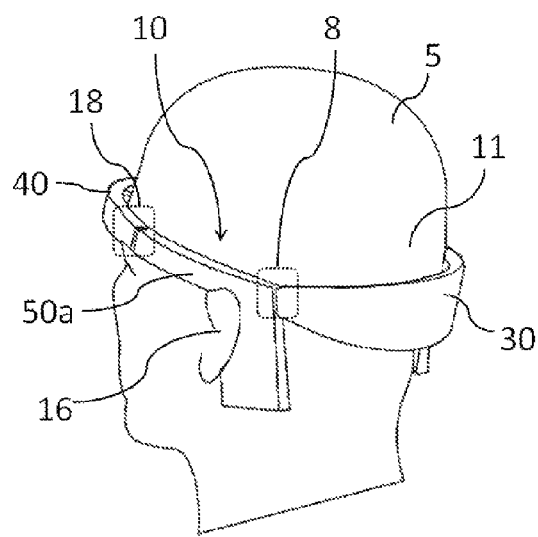
Fig. 1  Fig. 1A
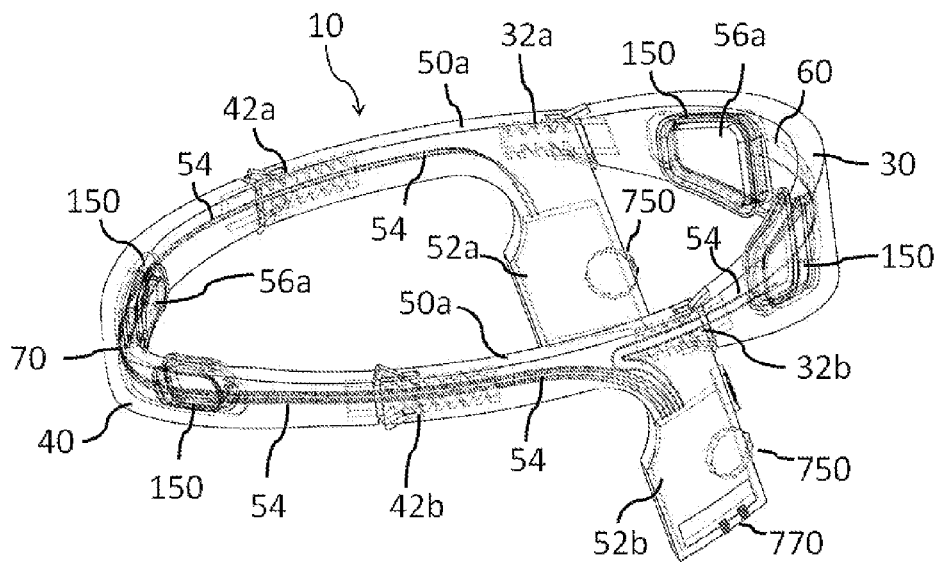
Fig. 2

HEADSET FOR TREATMENT AND ASSESSMENT OF MEDICAL CONDITIONS

REFERENCE TO RELATED APPLICATION

The present application is a Continuation In Part of PCT Application Publication Number WO2014/141213, filed 15 Mar. 2014 and entitled "HEADSET FOR TREATMENT AND ASSESSMENT OF MEDICAL CONDITIONS", which gains priority from U.S. Provisional Application No. 61/786,701 filed on 15 Mar. 2013, both of which are hereby incorporated by reference as if fully set forth herein.

FIELD OF THE INVENTION

The present invention relates to apparatus and methods for applying electrical stimulation to the head region, to headsets having electrodes for treatment of medical conditions using non-invasive electrical stimulation, to headsets adapted to assess medical conditions, and to electrode arrangements for use with such headsets.

SUMMARY OF THE INVENTION

According to some teachings of the present invention there is provided a headset for use in delivering electrical stimulation to a skin surface of a head of a user, the headset including: (a) a circumferential headset body, the body having a monolithic frame adapted to circumferentially fit around the head of the user, the body housing an electric circuit adapted to be connected to a power source; the headset body including an elastic arrangement, disposed on at least a portion of a circumference of the headset body; the elastic arrangement adapted to be tensioned along the circumference; (b) at least one electrode base, mechanically and at least semi-rigidly connected to the headset body, and electrically associated with the electric circuit, the electrode base adapted to receive at least one electrode pad; the headset body and the base adapted to orient an electrical stimulation surface of the pad towards the skin surface, during donning by the user; the elastic arrangement adapted such that, during the donning, the elastic arrangement radially urges the electrode base towards the skin surface such that the electrode pad makes physical and electrical contact with the skin surface; the elastic arrangement and the electrode base adapted such that for various degrees of tensioning of the elastic arrangement, a circumferential position of the electrode base, with respect to the frame, is fixed in a unique position.

According to another aspect of the present invention there is provided an electrode pad including: (a) a liquid-absorbent layer having a biocompatible, conductive contact surface, the contact surface adapted to be juxtaposed against the skin surface; (b) an electrically conductive layer having a broad first face attached to the liquid-absorbent layer, the conductive layer containing a carbon foil or carbon film, the conductive layer adapted to transfer an electrical current from a broad second face, distal to the first face, to the liquid-absorbent layer, via the first face, the liquid-absorbent layer and the electrically conductive layer forming an integral structure.

According to yet another aspect of the present invention there is provided an electrode base having: (a) a housing including a floor, and a flexible circumferential member surrounding the floor, and having a flexible circumferential wall extending generally above a perimeter of the floor, the wall ending in a circumferential rim; the floor and the flexible circumferential member forming a cavity adapted to receive an electrically conductive electrode pad; and (b) an electrically conductive material, disposed at least partially above, or within, the floor; the conductive layer adapted to be electrically associated to an electrical circuit, by means of an electrical conductor, and, when the pad is inserted, to electrically communicate, in an operational mode, with the electrode pad; the rim and the flexible circumferential wall adapted such that a pressure exerted against the electrode base, generally perpendicular to the rim, and towards a skin surface of a user, urges the rim against the skin surface, to substantially fluidly seal between the cavity and an ambient or external environment.

According to yet another aspect of the present invention there is provided a biocompatible electrode for juxtaposing against a skin surface of a user, the electrode including: (a) a liquid-absorbent layer having a biocompatible contact surface, the contact surface adapted to be juxtaposed against the skin surface; (b) an electrode backing, attached to the liquid-absorbent layer, the backing containing at least one electrically conductive material or element, the conductive material or element being electrically connected, in an operational mode, with the liquid-absorbent layer, when the liquid-absorbent layer is filled with liquid; the biocompatible contact surface having: (i) a long dimension ($D_L$) having a maximum length of 20 mm to 55 mm; (ii) a narrow dimension ($D_N$) having a maximum length of 10 mm to 25 mm; a first side of a perimeter of the biocompatible contact surface having a generally concave contour having a concavity defined by first and second boundary points disposed at opposite ends of the concavity, wherein:

$$A/L \geq 0.5 \text{ mm}$$

A being an area bounded by the line and the concavity; L being a length of a line between the boundary points; the length (L) being at least 10 mm; a line disposed between a first point on the concave contour and a second point on the perimeter, on a side opposite the concave contour, and aligned in perpendicular fashion with respect to the contour at the first point, having a length H, and wherein, over an entirety of the concave contour, $$H_{max}/H_{min} \leq 2.5,$$

$H_{max}$ being a maximum value of H over the entirety; and $H_{min}$ being a minimum value of H over the entirety.

According to yet another aspect of the present invention, there are provided methods of donning and positioning the headset on the head of the user, substantially as described herein.

According to further features in the described preferred embodiments, the circumferential headset body has a front section adapted to fit around a front portion of the head, and the at least one electrode base is a front electrode base disposed on the front portion.

According to still further features in the described preferred embodiments, the front section is a front mechanical element that is physically distinct from the circumferential headset body.

According to still further features in the described preferred embodiments, the front mechanical element spans at most 40%, at most 35%, at most 30%, or at most 20%, of a circumference of the circumferential headset body.

According to still further features in the described preferred embodiments, the front mechanical element spans within a range of 10% to 40%, 15% to 40%, 20% to 40%, 25% to 40%, or 25% to 35%, of a circumference of the circumferential headset body.

According to still further features in the described preferred embodiments, the circumferential headset body has a rear section adapted to fit around a rear portion of the head, and the at least one electrode base includes a rear electrode base disposed on the rear portion.

According to still further features in the described preferred embodiments, the rear section is a rear mechanical element that is physically distinct from the circumferential headset body.

According to still further features in the described preferred embodiments, the rear mechanical element spans at most 40%, at most 35%, at most 30%, or at most 20%, of a circumference of the circumferential headset body.

According to still further features in the described preferred embodiments, the rear mechanical element spans within a range of 10% to 40%, 15% to 40%, 20% to 40%, 25% to 40%, or 25% to 35%, of a circumference of the circumferential headset body.

According to still further features in the described preferred embodiments, the front and rear mechanical elements span, in total, 45% to 75%, 50% to 75%, 55% to 75%, or 55% to 70%, of the circumference.

According to still further features in the described preferred embodiments, the frame includes at least semi-rigid side components, bi-laterally disposed on the frame, and forming side portions of the circumference of the headset body.

According to still further features in the described preferred embodiments, the side components span, in total, 15% to 50%, 20% to 50%, 25% to 50%, 30% to 50%, 35% to 50%, or 30% to 45%, of the circumference.

According to still further features in the described preferred embodiments, each of the side components has an element disposed generally perpendicular to the circumference, and adapted, in a donned mode, to fit behind an ear of the user.

According to still further features in the described preferred embodiments, the circumferential rigidity of the side components exceeds a circumferential rigidity of the front section and the rear section.

According to still further features in the described preferred embodiments, the circumferential elasticity of the front section and the rear section exceed a circumferential elasticity of the side components.

According to still further features in the described preferred embodiments, the frame includes a positioning system for angular and longitudinal positioning of the headset body, the positioning system including at least one at least semi-rigid side component, the side component having: a first, elongated element, forming a portion of the circumference, and adapted to fit above an ear of the user, to determine the longitudinal positioning, and a second element disposed generally perpendicular to the elongated element, and adapted to fit behind the ear, to determine the angular positioning of the headset body.

According to still further features in the described preferred embodiments, the frame includes at least a first bi-lateral size adjustment mechanism adapted to fixedly adjust the circumference of the headset body.

According to still further features in the described preferred embodiments, the adjustment mechanism is rigid or at least semi-rigid.

According to still further features in the described preferred embodiments, the frame includes first and second bi-lateral size adjustment mechanisms adapted to adjust the circumference of the headset body, the first adjustment mechanism connecting the side components to the front section, and the second adjustment mechanism connecting the side components to the rear section.

According to still further features in the described preferred embodiments, the first and second adjustment mechanisms are adapted to enable adjustment of the circumference of the headset body while a circumferential position of the side components remains fixed.

According to still further features in the described preferred embodiments, the frame is adapted such that along at least 30%, at least 40%, at least 50%, or at least 60% of a length of the circumference, the frame is substantially non-elastic.

According to still further features in the described preferred embodiments, the headset body is adapted to juxtapose a contact surface of an electrical device opposite or against the skin surface, the elastic arrangement adapted to radially urge the electrical device towards the skin surface such that a contact surface of the electrical device makes physical contact with the skin surface; the elastic arrangement adapted such that for various degrees of tensioning of the elastic arrangement, a circumferential position of the electrical device is fixed in a unique position.

According to still further features in the described preferred embodiments, the electrical device includes a sensor adapted to sense a body parameter associated with the head of the user.

According to still further features in the described preferred embodiments, the liquid-absorbent layer of the electrode pad includes at least one material selected from the group consisting of a non-woven fabric, felt or sponge.

According to still further features in the described preferred embodiments, the electrically conductive layer has, on a second face, distal to the liquid-absorbent layer, an electrically conductive layer having a higher electrical conductivity than the bulk of the electrically conductive layer, this highly conductive layer typically being an electrically conductive paint, preferably disposed in a mesh pattern.

According to still further features in the described preferred embodiments, the liquid-absorbent layer and the electrically conductive layer having the layer of electrically conductive paint form an integral structure.

According to still further features in the described preferred embodiments, the conductive carbon film or carbon foil has a resistivity of 1-180 ohm/square or 30-100 ohm/square.

According to still further features in the described preferred embodiments, the conductive carbon film or carbon foil has a thickness within a range of 30-1500 microns or 50-200 microns.

According to still further features in the described preferred embodiments, on the rim of the electrode base are circumferentially disposed a plurality of sealing fingers containing a volume, the sealing fingers adapted such that, when the rim is urged against the skin surface, the plurality of sealing fingers substantially seal between the volume and a volume external to the sealing fingers.

According to still further features in the described preferred embodiments, the rim includes, or consists essentially of, a circumferentially disposed plurality of sealing fingers, the sealing fingers adapted such that, when pressure is exerted, in generally perpendicular fashion with respect to the electrode base floor, or to the skin surface, the plurality of sealing fingers substantially seal between the cavity and a volume external to the rim.

According to still further features in the described preferred embodiments, the ratio A/L of the electrode arrangement is at least 0.2 mm, at least 0.5 mm, at least 0.7 mm, at least 1 mm, at least 1.5 mm, or at least 1.7 mm.

According to still further features in the described preferred embodiments, the length (L) is at least 12 mm, at least 15 mm, at least 18 mm, or at least 20 mm.

According to still further features in the described preferred embodiments, the electrode arrangement further includes an electrode pad.

According to still further features in the described preferred embodiments, an inner surface of the flexible circumferential wall has a radial curvature, and a radial distance between an inner surface of the rim, and a most radially inward point of the inner surface of the wall, is at least 1 mm, at least 3 mm, at least 5 mm, or at least 10 mm.

According to still further features in the described preferred embodiments, this radial distance is within a range of 1 to 15 mm, 2 mm to 12 mm, 2 mm to 10 mm or 2 mm to 7 mm.

According to still further features in the described preferred embodiments, an outer surface of the flexible circumferential wall has a radial curvature, and wherein a length of the curvature of the outer surface is at least 1 mm, at least 2 mm, at least 3 mm or at least 5 mm.

According to still further features in the described preferred embodiments, a length of the curvature of this outer surface is within a range of 1 mm to 15 mm, 2 mm to 10 mm or 3 mm to 8 mm.

According to still further features in the described preferred embodiments, the electrode arrangement further includes a pressuring arrangement, mechanically associated with the electrode base, and adapted to deliver the pressure against the electrode base, generally perpendicular to the rim.

According to still further features in the described preferred embodiments, the electrical device includes a transmitting arrangement adapted to transmit a signal from the sensor.

According to still further features in the described preferred embodiments, the electrode base housing includes a flexible bellows-type member.

According to still further features in the described preferred embodiments, the electrode base housing includes a liquid trapping and storing arrangement.

BRIEF DESCRIPTION OF THE FIGURES

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like functionalities, but not necessarily identical elements.

In the drawings:

FIGS. 1 and 1A provide perspective views of one embodiment of the inventive headset, positioned on a head of a user;

FIG. 2 is a perspective view of one embodiment of the inventive headset;

DETAILED DESCRIPTION

Figure 3:
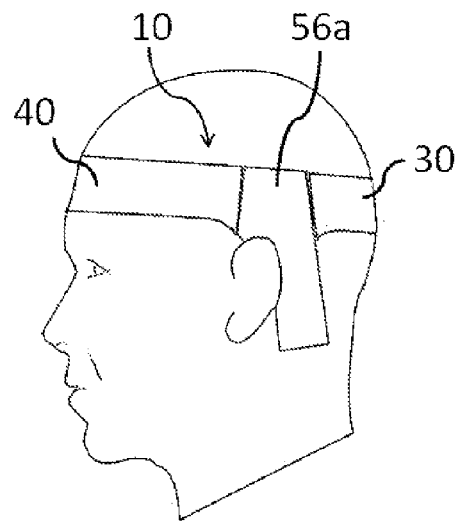
FIGS. 3 and 4 respectively provide a side view of inventive headsets, positioned on a head of a user.

Device and methods are described herein that include a headset with one or more integrated electrodes for applying electrical stimulation to peripheral nerves, cranial nerves and brain regions. The inventive headset is a head mounted construction that can be served as a platform for applying electrical stimulation to treat various conditions such as migraine and tension headaches, fibromyalgia, depression, post-traumatic stress syndrome, anxiety, obsessive compulsive disorder (OCD), insomnia, epilepsy, attention deficit hyperactivity disorder (ADHD), Parkinson's disease, Alzheimer's disease, multiple sclerosis, and stroke. The inventive headset may facilitate motor and cognitive learning and may induce relaxation. The inventive headset may also serve as a platform for various sensors, in order to detect and/or assess various conditions.

The stimulation electrodes and the quality of its contact with the scalp are a fundamental aspect in the functionality of the invented apparatus. Ensuring optimal conductivity between the electrodes and the scalp is essential for proper transfer of the electrical current to the target tissues, which is the basis for an effective treatment. Improper conductivity may result in failure of the therapy, unpleasant sensation and even skin irritation due to "hot spots" of high current density. The inventors have also found that non-invasive application of electrical current to the head region, no matter which indication it is applied for, may pose numerous challenges including stimulation in the presence of hair, high level of sensory sensitivity of the scalp and forehead, the criticality of robust contact and electrical conductivity between the electrodes and the scalp, despite variations in head size and contours, and accurate placement of the stimulating electrodes above the target nerve and brain regions.

Several aspects of the present invention relate to features that are aimed at ensuring that the electrical current is properly delivered from the electrode to the target tissues and for treating and assessing the head region in an effective and comfortable manner.

With reference now to the drawings, FIG. 1 and FIG. 1A provide perspective views of one embodiment of the invented headset system 10, donned on head 5. In one embodiment, headset 10 may be configured to include a circumferential frame ("headset body") that may include a posterior elastic member 30, an anterior elastic member 40 and bilateral semi rigid and preferably rigid members 50a. Posterior elastic member 30 may be configured to be coupled to bilateral members 50a at connection point 8 and 16. Anterior member 40 may be configured to be coupled to bilateral members 50a at connection points 14 and 18. Anterior member 40 may be configured to encompass the forehead region 12. Posterior elastic member 30 may be configured to encompass the occiput region 11. Middle bilateral semi-rigid members 50a nay be configured to be positioned behind and above ears 16.

FIG. 2 illustrates a perspective view of one embodiment of the invented headset system 10. Headset 10 may be configured to include an elastic posterior member 30, elastic anterior member 40 and rigid and preferably semi-rigid bilateral members 50a. Posterior member 30 may be configured to connect to middle bilateral members 50a by size adjustment mechanisms 32a and 32b, configured to be located behind the ears. Anterior member 40 may be configured to connect to bilateral middle members 50a by size adjustment mechanisms 42a and 42b, configured to be located at both sides of the head, anterior to the ears.

The adjustment of headset 10 to various head sizes may be performed by bilateral anterior adjustment mechanisms 32a and 32b and posterior bilateral adjustment mechanisms 42a and 42b. Pulling or pushing elastic members 30 and 40 away from or toward middle bilateral members 50a, allows increasing or decreasing the size/circumference of headset 10. According to certain embodiment, middle bilateral members 50a may be configured to be flexible in order to self-align to a wide variety of head contours.

The mechanism for adjustment of headset 10 to various head sizes may include solely bilateral anterior adjustment mechanisms 32a and 32b, or bilateral posterior adjustment mechanisms 42a and 42b.

In some embodiments, having both anterior adjustment mechanisms 32a and 32b and posterior adjustment mechanisms 42a and 42b may enable better adjustment of the headset while maintaining its symmetrical placement on the head. Furthermore, it may enable adjustment of the headset size while maintaining the proper placement of bilateral members 50a behind the corresponding ears.

Posterior member 30 and anterior member 40 may be configured to contain electrode bases (also called electrode system) 60 and 70 respectively and when stretched, are configured to apply radial force on electrode base housing 150 toward the scalp in order to ensure electrical coupling between electrodes pads 56a and the skin surface, while minimizing undesired pressure of the headset against the scalp at areas that does not hold the electrodes.

Middle bilateral member 50a may be configured to contain electronic circuit 52b, which may be configured to be electrically coupled by conductive wires 54 to battery 52a and to electrodes units 60 and 70.

Electronic circuit 56b may be configured to include a stimulation circuit, a microprocessor, a charging circuit and a user interface.

The stimulation circuit may be configured to produce biphasic, charged balanced electrical pulses, mono-phasic electrical pulses, and/or direct current stimulation.

According to still further features of the described preferred embodiments, the stimulation circuit may be configured to produce electrical stimulation within an intensity range of 0-80 mA, 0-40 mA, 0-20 m, or 0-15 mA.

According to still further features of the described preferred embodiments, the stimulation circuit may be configured to produce stimulation pulses with a duration of 10-600 μsec, 50-500 μsec, 100-500 μsec, 100-450 μsec, 150-400 μsec or 150-450 μsec.

According to still further features of the described preferred embodiments, the stimulation circuit may be configured to produce stimulation pulses at a frequency of 1-500 Hz, 10-300 Hz, 10-250 Hz, 20-180 Hz or 30-180 Hz.

According to still further features of the described preferred embodiments, headset 10 may be configured to connect to an external electronic and stimulation circuit and thereby to transfer electrical current from the external stimulator to the headset electrodes. Headset 10 may be configured to connect to at least one external electrode that may be located at various areas of the body. Headset 10 may be configured to connect to an external electronic circuit and processor in order to transfer signals from its on board sensors to the external processor.

Battery 52a may be recharged by plugging a charger to charging port 770 located on member 50a. Bilateral member 50a may also be configured to include user controls and interface 750. In some embodiments, both bilateral members may be configured to include a user interface 750. In some embodiments, other parts of inventive headset 10, such as anterior member 40 or posterior member 30, may be configured to include user interface 750.

In some embodiments of the present invention, elastic members 30 and 40 of headset 10 may be configured, in a stretched mode, to transfer radial force to electrode base housing 150 in order to ensure contact between electrode pads 56a and the skin surface, while minimizing undesired pressure of the headset against the scalp at areas that does not hold the electrodes.

FIG. 3 is an illustration of a side view of headset 10. In some embodiments, headset 10 may be configured to be positioned at a higher location on the head while maintaining its various properties including accurate placement, adjustment to various head sizes and electrode attachment. Positioning headset 10 at a higher location on the head may enable stimulation of other nerves and brain regions, and may also enable positioning of various sensors, such as for example EEG sensors, at higher locations over the head.

According to another aspect of the present invention, headset 10 may be configured to include wider elastic members 40 and 30, with bilateral member 56a that may be adapted to connect to wider members 40 and 30. Wider members 40 and 30 may enable integration of larger electrodes within headset 10 in order to stimulate larger areas, such as for stimulation of various brain regions.

Figure 4:
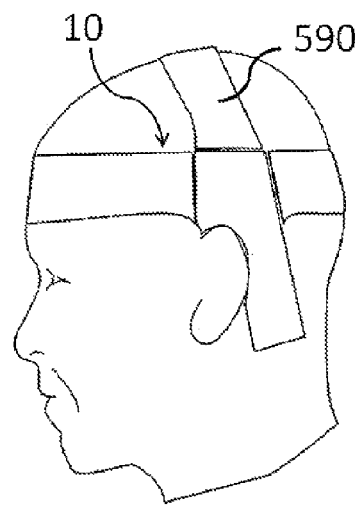

FIG. 4 provides a side view of headset 10, having additional semi-rigid and preferably elastic member 590, configured to be coupled perpendicularly to bilateral member 56a and adapted to be disposed between bilateral members 56a and to encompass the top of the head. Elastic member 590 may enable stimulation and positioning of electrodes and sensors at higher locations on the head.

Figure 5:
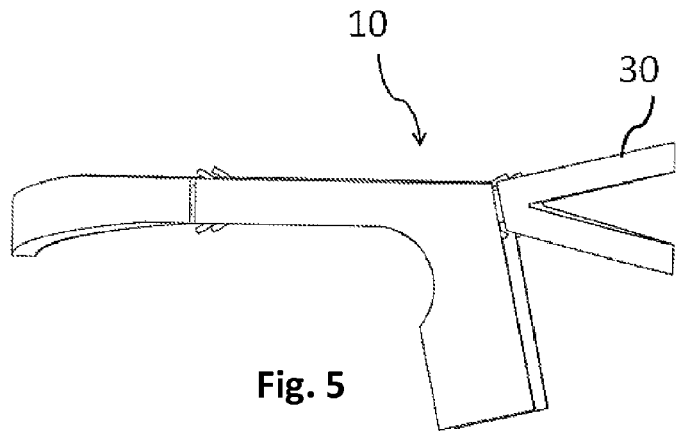
FIG. 5 is a side view of a portion of an inventive headset having a bifurcated posterior elastic member for improved headset stability.

FIG. 5 provides a side view of headset 10, configured to include a bifurcated posterior elastic member 30 in order to increase the stability of headset 10 over the occiput region.

Figure 6:
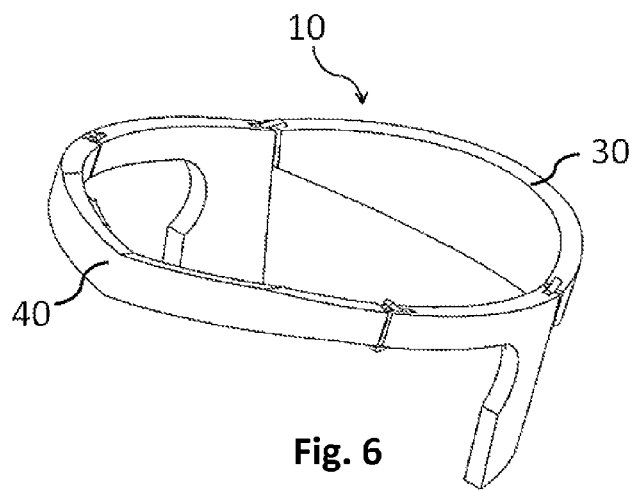
FIG. 6 is a perspective view of an inventive headset having a posterior elastic member devoid of electrodes.

FIG. 6 is a perspective view of headset 10, where posterior elastic member 30 does not hold electrodes and its main or sole function is to stabilize headset 10 on the head.

When required, anterior elastic member 40 may be configured to not include electrodes while posterior member 30 includes the electrodes.

Figure 7:
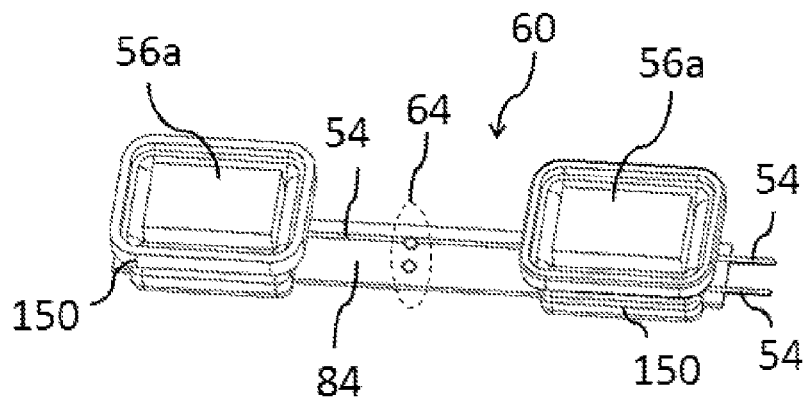
FIGS. 7 and 7A provide perspective views of an inventive electrode base arrangement, and an elastic member for housing this arrangement, according to one embodiment of the present invention.
Figure 7A:
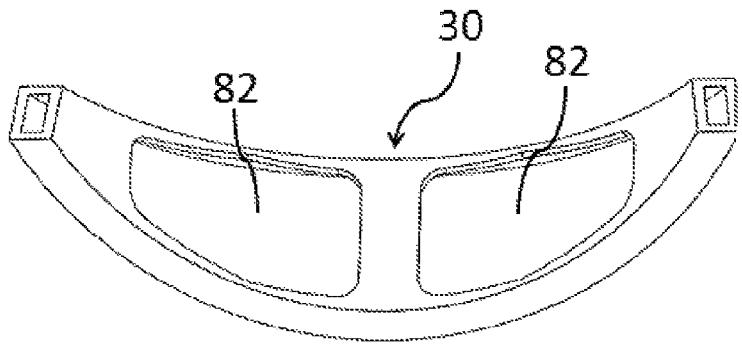

FIG. 7 provides a perspective view of an inventive electrode base or base arrangement 60; FIG. 7A provides a perspective view of an elastic member 30 for housing arrangement 60, according to one embodiment of the present invention.

With reference to FIGS. 7 and 7A, elastic member 30 is configured to be at least partially hollow in order to contain electrode base 60 and electrical conducting wires 54, as well as to assist in preserving a stable three-dimensional configuration of the headset while maintaining a low modulus of elasticity. Elastic member 30 may be configured to include at least one opening 82 on an interior side (facing the skin surface). Electrode base 60 may be configured to include at least one housing 150. In one embodiment, housing 150 is configured to be coupled to elongated flexible member 64. Electrode base 60 may be configured to be physically coupled inside elastic member 30, such that a flexible connecting band 84 is coupled to elastic member 30 at coupling portion 64.

Elastic member 30 may have a lower modulus of elasticity above electrode base housing 150, compared to a higher modulus of elasticity in its other areas. A lower modulus may be achieved in areas of member 30 that are parallel to the bottom surface of housing 150, due to opening 82 and, for example, due to configuring the external surface of member 30, in the area parallel to openings 82, to be thinner than its other areas. Thus, when headset 10 is donned, a focal radial force is applied by member 30 on electrode base housing 150 toward the scalp. In contrast, other areas of elastic member 30 may be configured to have a higher modulus of elasticity and therefore the radial force toward the scalp at these areas is minimized in order to prevent excess pressure where not needed. The areas which are configured to have a higher modulus of elasticity may also assist in maintaining a stable three-dimensional structure of member 30 and of headset 10, thereby facilitating easier donning and accurate placement of the electrodes.

Figure 8:
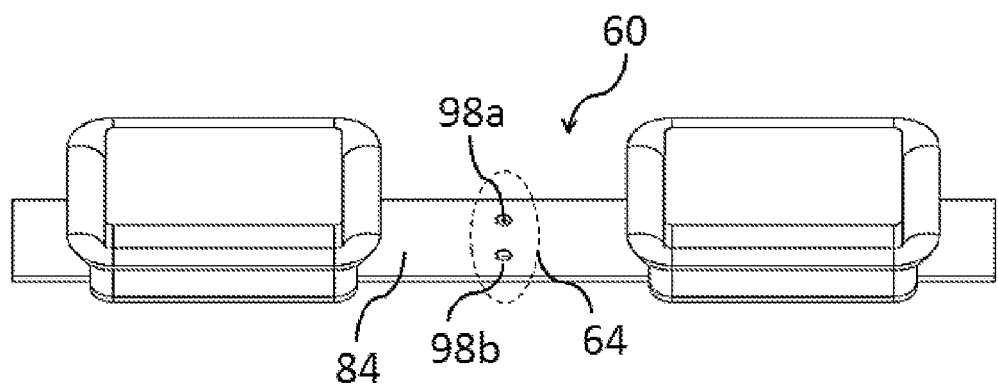
FIG. 8 provides a perspective view of an inventive electrode base arrangement, according to a particular embodiment of the present invention.
Figure 8A:
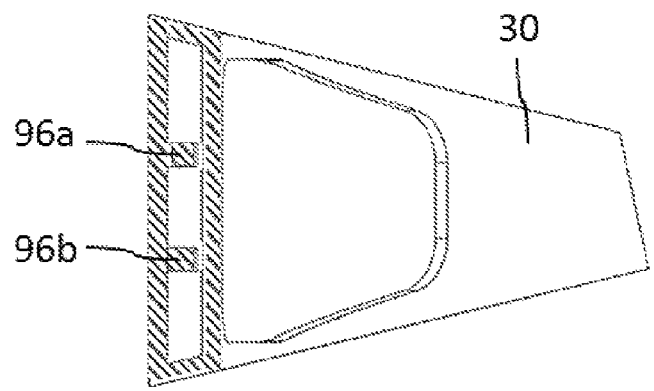
FIG. 8A provides a perspective view of the elastic member shown in FIG. 7A with a cross section at a middle portion thereof.

FIG. 8 and FIG. 8A provide a perspective view of electrode base 60 and a cross-sectional view of elastic member 30 (shown in FIG. 7A), respectively. In order to enable coupling to electrode base 60, elastic member 30 may be configured to include protrusions 96a and 96b. Electrode base 60 may be configured to include holes 98a and 98b in flexible connecting band 84. In order to physically couple electrode base 60 and elastic member 30, electrode base 60 may be inserted into elastic member 30, such that protrusions 96a and 96b may be snapped into holes 98a and 98b. The physical coupling may include other mechanisms. For example, flexible member 68 may be glued at its coupling portion 64 to flexible member 30.

Figure 9:
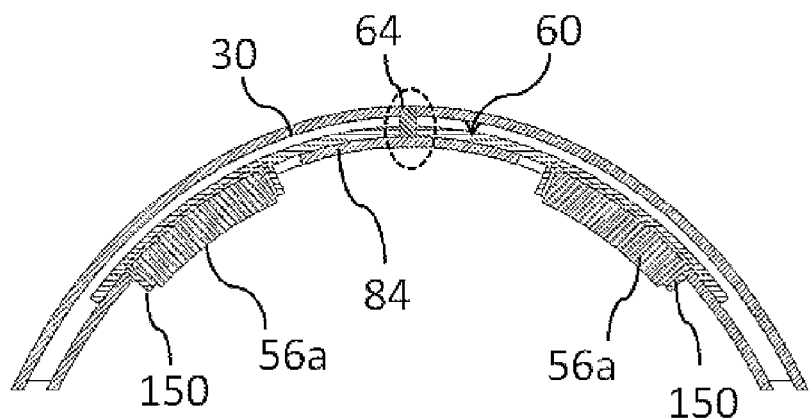
FIG. 9 is a cross-sectional view of the electrode base of FIG. 7, coupled inside the elastic member of FIG. 7A.

FIG. 9 provides a cross-sectional view of electrode base 60, coupled inside elastic member 30. Electrode base 60 may be integrated inside headset member 30 where flexible connecting band 84 may be physically coupled to elastic member 30 at coupling portion 64 only, and therefore, when the headset is donned, member 30 may be stretched to elicit radial force on electrode base housing 150 and electrode pads 56a toward the scalp, without being constrained by electrode system 60. This arrangement also ensures that when headset member 30 is stretched, the pre-determined distance between electrode base housing 150 is maintained.

Figure 10:
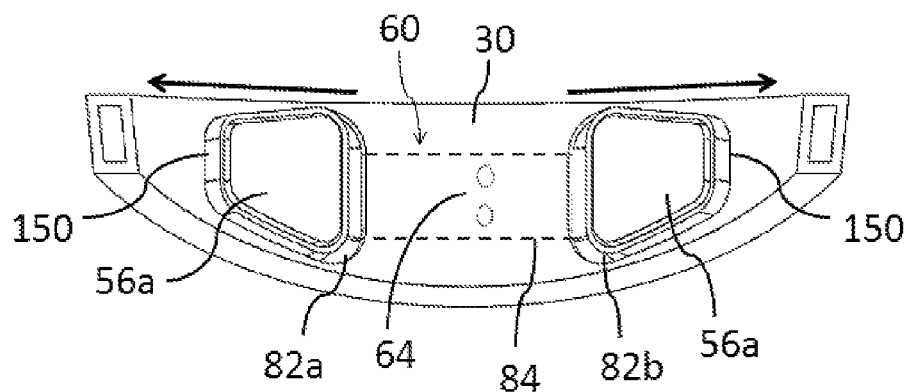
FIG. 10 provides a perspective view of the inventive structure shown in FIG. 9.

FIG. 10 illustrates a portion of headset member 30 according to one embodiment. Electrode system 60 (partially hidden) is integrated inside member 30 while only electrode base housing 150 and electrode pads 56a protrude through openings 82a and 82b of elastic member 30. Flexible connecting band 84 and coupling portion 64 are illustrated by dotted lines. Openings 82a and 82b may extend beyond the medial edge of electrode base housings 150 in order to allow openings 82a and 82b to extend laterally when member 30 is stretched and therefore the extension of member 30 may not be constrained.

Figure 11A:
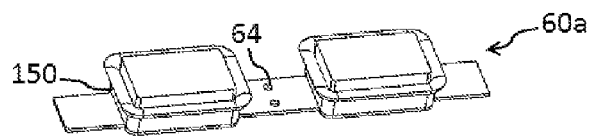
FIGS. 11A-11C illustrate an inventive, adjustable electrode base arrangement for adjusting the distance between adjacent electrode base housings, and three different positionings of those electrode base housings.
Figure 11B:
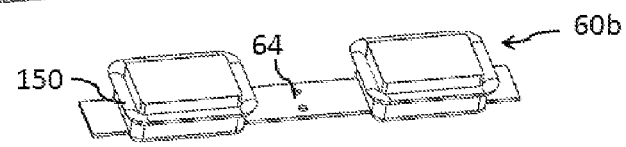
Figure 11C:
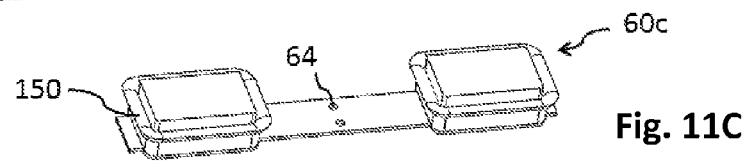
Figure 11D:
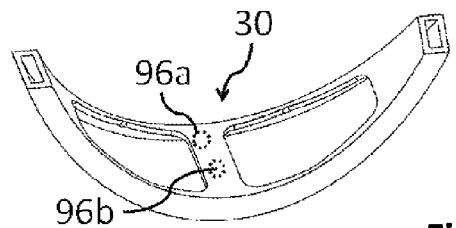
FIG. 11D provides a perspective view of an elastic member for housing the adjustable electrode base arrangement shown in FIGS. 11A-11C.

FIGS. 11A-11C are perspective views of an inventive electrode base arrangement in which the distance between adjacent electrode base housings 150, may be pre-set. FIGS. 11A-11C provide three different pre-set positionings 60A-60C of those electrode base housings. FIG. 11D provides a perspective view of an elastic member for housing the adjustable electrode base arrangement shown in FIGS. 11A-11C.

According to certain features of the described preferred embodiments, the position of electrode base housing 150 may be adjusted to fit various morphological and anthropometric variables of certain users. According to one embodiment, electrode base units 60a, 60b and 60c may be configured to have a variable distance between its electrode base housing 150. It may be configured to be reversibly coupled to elastic member 30 by holes 64 of the electrode system and protrusions 96a and 96b (both hidden) on elastic member 30. According to certain features of the described preferred embodiments, coupling of electrode base units 60a, 60b and 60c may also be performed by other coupling mechanisms.

Figure 12:
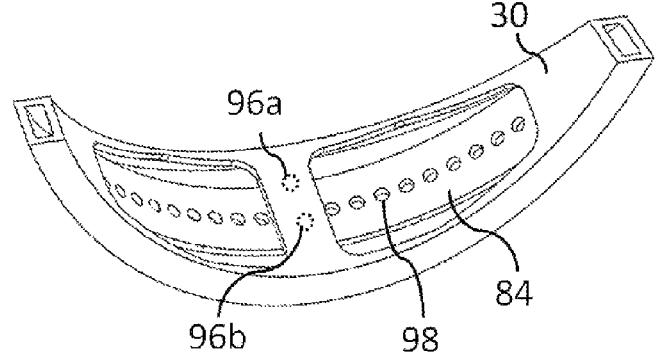
FIGS. 12 and 13 illustrate an adjustable electrode base housing arrangement, and an elastic member for housing this arrangement, according to one embodiment of the present invention.
Figure 13:
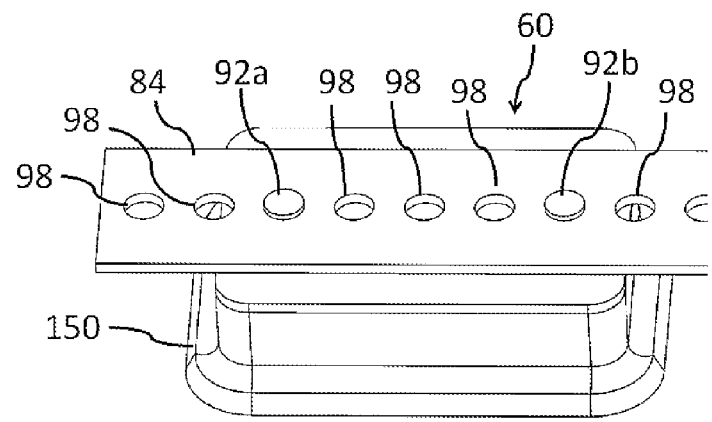

FIG. 12 and FIG. 13 illustrate a mechanism for adjustment of the placement of electrode base housing 150 according to further features of the described preferred embodiment.

FIG. 12 illustrates an interior view of elastic member 30 according to one embodiment, where flexible connecting band 84 is coupled to member 30 by protrusions 96a and 96b (both hidden) elongating from member 30 and snaped into holes in flexible connecting band 84. The mechanical coupling of flexible connecting band 84 and elastic member 30 may be performed by other mechanisms such as other snap connectors or by gluing. According to one embodiment, flexible connecting band 84 is configured to include holes 98 at a distance within a range of 0.5-5 cm between each hole, and more typically, within 0.5-3 cm, 0.5-2 cm, or 0.5-1 cm.

FIG. 13 illustrates a bottom view of a portion of electrode base 60. According to one embodiment, electrode base housing 150 may be configured to include protrusions 92a and 92b arising from its bottom surface. Protrusions 92a and 92b are configured to be snaped into any of the holes 98 in flexible connecting band 84. The placement of electrode base housing 60 may be adjusted by snapping protrusions 92a and 92b into other holes 98 in flexible connecting band 84.

Figure 14:
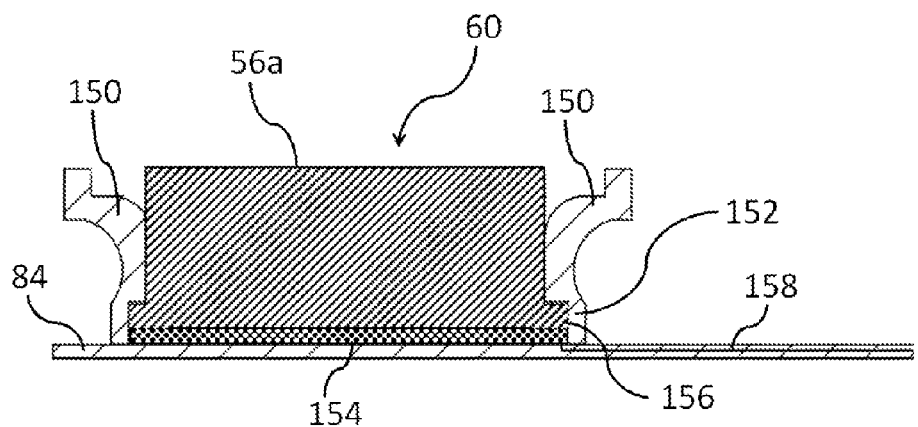
FIG. 14 is a cross-sectional view of an electrode pad disposed an electrode base.

FIG. 14 is a cross section of an electrode pad 56a disposed in an electrode base 60. Electrode base 60 may be configured to be physically coupled to the headset by elongated flexible connecting band 84 and may be electrically coupled to the headset electrical circuit by conductive wire 158. It may be configured to include at least one electrode base housing 150 which include elevated circumferential walls that are surrounding a "floor", thereby creating a cavity adapted to receive at least one conductive electrode pad 56a. According to certain embodiment, electrode base housing 150 is preferably made of a flexible material such as silicon or thermoplastic polyurethane (TPU).

Electrode base housing 150 may be configured to include an electrically conductive material 154 disposed at least partially above, or within electrode base housing 150 floor. The conductive layer is adapted to be electrically coupled to an electric circuit by electrical conductor 158.

Conductive layer 154 may be configured to include material such as stainless steel, copper, brass, silicone carbon, conductive silver paint print, stainless mesh or other conducting elements. When conductive layer 154 is made of carbon, an additional layer of conductive paint may be printed on its bottom surface. Such a conductive paint layer may improve the homogeneity of current distribution across the surface of conductive layer 154 and thereby improve the homogeneity of current distribution on the surface of electrode pad 56a. Conductive layer 154 may preferably be flexible in order to not compromise the overall flexibility of electrode base 60 and thereby to ensure its alignment with various head contours. In certain embodiments, conductive layer 154 may be limited in its area and may be configured to cover only a portion of the floor surface of electrode base housing 150. In such a case, conductive layer 154 may not be flexible and may be made of various electrically conductive materials known to those of skill in the art. Conductive layer 154 may be configured to be electrically coupled to an electrical conductor (cable or wire) 158 and thereby be electrically connected to the headset electrical circuit.

Electrode pad 56a may be configured to be releasably coupled (physically and electrically) to electrode base housing 150. Electrode pad 56a may include at least a portion of water or other liquid absorbing material such as non-woven fabric, felt or sponge. When coupled to housing 150, electrode pad 56a is configured to be in electrical contact with conductive layer 154. When the headset is donned, pad 56a is urged toward the skin surface and may create electrical contact with the skin surface (skin surface including the scalp) in order to transfer electrical current to the skin surface.

In some embodiments, the electrode pad 56a may be provided to the user dry, and the user may soak electrode pad 56a with water, saline, conductive gel, or any other suitable liquid before use. In other embodiments, the electrode pad 56a may be pre-soaked with conductive gel, such that the gel is mostly absorbed in the pad, and the user need not soak the pad at all. The conductive gel may be any commercially available conductive gel suitable for use with electrodes. It is appreciated that use of conductive gel improves conductivity and reduces dehydration of the pad 56a, and that pre-soaked pads 56a may be easier and less messy for the user to handle.

Electrode pad 56a and other electrodes associated with the headset may be configured to receive (sense) electrical current or other bio-signals from the skin surface, such as for example electroencephalogram (EEG) and either transfer it via the headset circuit to an electronic circuit that includes a microprocessor or transmit it wirelessly to a remote unit.

Electrode pad 56a may be disposable and may be conveniently replaced by the user.

Electrode pad 56a may be configured to include a peripheral edge 156 that is thinner than the central area of pad 56a. Peripheral edge 156 can be made by various manufacturing process such as ultrasonic welding, RF welding or heat compression. By inserting the thin edge 156 into a corresponding groove 152 in housing 150, electrode pad 56a can be reversibly physically coupled to housing 150 and electrically coupled to conductive layer 154.

Electrode pad 56a may be configured to have larger area compared to housing 150. It can therefore be squeezed into housing 150 in order to be reversibly (physically an electrically) coupled to housing 150.

Electrode base housing 150 may be configured to include a conducting mechanical snap connector configured to be both physically and electrically reversibly coupled to a corresponding connector attached to electrode pad 56a.

Figure 15A:
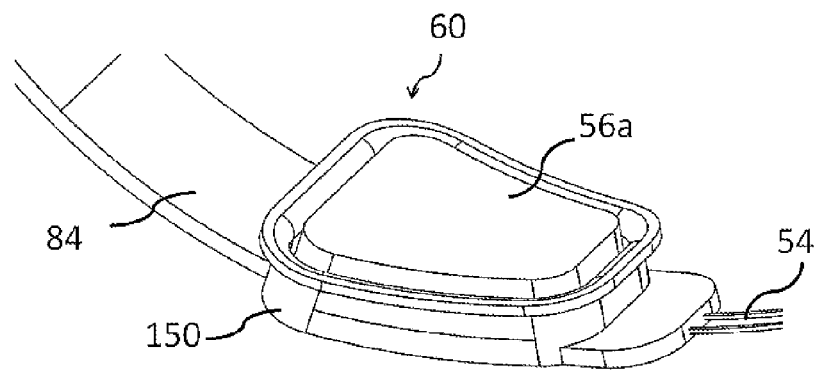
FIGS. 15A and 15B provide perspective views of an electrode base with (FIG. 15A) and without (FIG. 15B) a multi-layered electrode pad, according to the present invention.
Figure 15B:
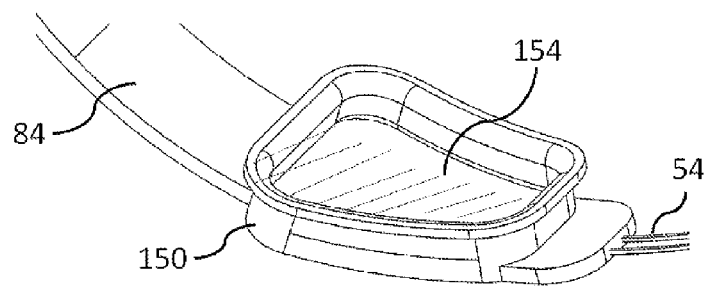
Figure 15C:
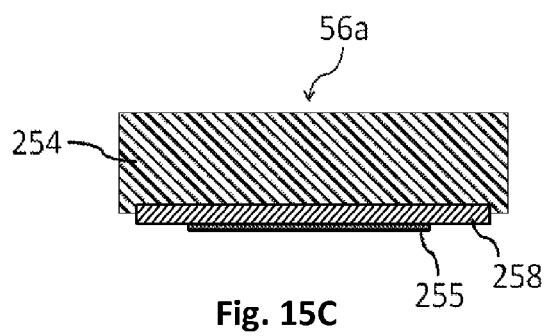
FIG. 15C and FIG. 15D provide cross-sectional and bottom views of this multi-layered electrode pad.
Figure 15D:
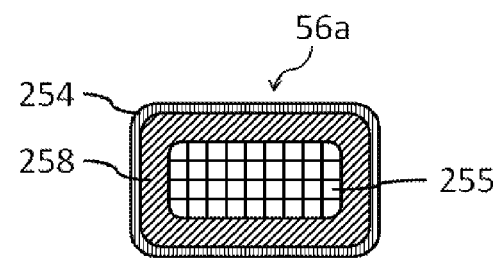

Perspective views of an electrode base 60 with and without an inventive, multi-layered electrode pad 56a are provided in FIG. 15A and FIG. 15B. FIG. 15C and FIG. 15D provide cross-sectional and bottom views of multi-layered electrode pad 56a. Multi-layered electrode pad 56a may include liquid absorbent layer 254 and a flexible electrically conductive layer 258, preferably made of a carbon foil. The two layers may be attached or directly attached. Various manufacturing processes may be used, including heat welding, RF welding, ultrasonic welding, gluing or sewing. In order to reduce current density at the edges of liquid absorbing layer 254, conductive layer 258 may be configured to have a smaller area or "footprint" than layer 254. Consequently, the current density at the edges of layer 254 (which has a lower electrical conductivity with respect to layer 258) will be reduced. Conductive layer 258 may further include a thin electrically conductive layer 255 of conductive paint, which may be printed in a "mesh" pattern and may be configured to cover only the central portion of layer 258. Conductive layer 255 may preferably be printed on the bottom surface of layer 258 and may be configured to face conductive layer 154 of electrode base housing 150 so as to be electrically coupled when multi-layered electrode pad 56a is attached to electrode base housing 150. Conductive print layer 255 may be configured to have a higher electrical conductivity compared to layer 258, such that current dispersion over layer 258 is improved while reducing current density at the edges of layer 258 (which does not include layer 255).

FIGS. 16A, 17A, 18A, 19A, and 20A provide cross-sectional views of an electrode base assembly, in which a particular electrode pad structure is coupled to an electrode base housing, according to various embodiments of the present invention. FIGS. 16B, 17B, 18B, 19B, and 20B provide cross-sectional views of each respective electrode pad shown in FIGS. 16A, 17A, 18A, 19A, and 20A.

Figure 16A:
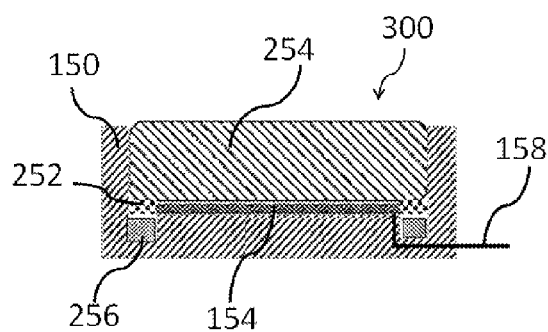
FIGS. 16A, 17A, 18A, 19A, and 20A provide cross-sectional views of an electrode base assembly, in which a particular electrode pad structure is coupled to an electrode base housing, according to various embodiments of the present invention.
Figure 16B:
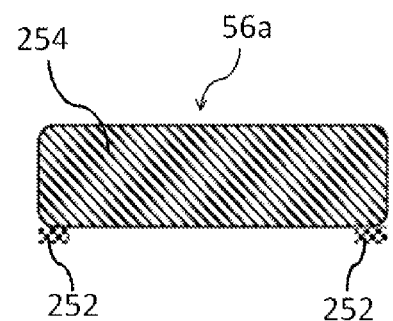
FIGS. 16B, 17B, 18B, 19B, and 20B provide cross-sectional views of each respective electrode pad shown in FIGS. 16A, 17A, 18A, 19A, and 20A.

With reference now to FIGS. 16A and 16B, electrode pad 56a may include a liquid absorbing layer 254 and a "hook" (e.g., Velcro®) fastening layer 252. Both layers may be attached by various manufacturing process such as heat welding, RF welding, ultrasonic welding, gluing or sewing. According to one embodiment, electrode base housing 150 may be configured to be coupled to a "loop" (e.g., Velcro®) fastening layer 256, disposed in a groove in the internal perimeter of elastic housing 150. According to one embodiment, in order to releasably couple electrode pad 56a to electrode base housing 150, the user may position electrode pad 56a inside housing 150 and thereby the hook layer 252 of electrode pad 56a and the loop layer 256 may be reversibly attached, ensuring contact between conducting layer 154 and liquid absorbing layer 254.

Figure 17A:
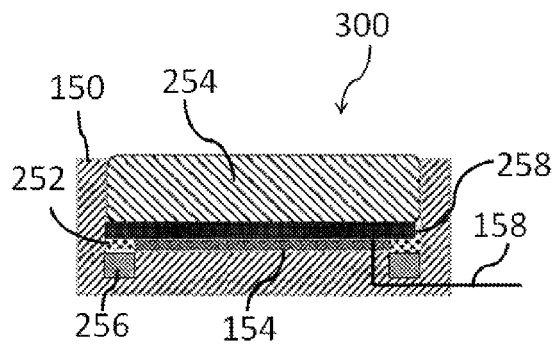
Figure 17B:
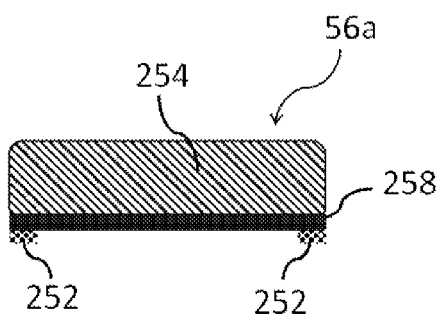

With reference now to FIGS. 17A and 17B, electrode pad 56a may include three layers: a liquid absorbing layer 254, a flexible conductive layer 258, preferably made of a flexible carbon layer and a "hook" (e.g., Velcro®) fastening layer 252, coupled to at least portion of the bottom perimeter of electrode pad 56a. The three layers may be attached by various manufacturing process such as heat welding, RF welding, ultrasonic welding, gluing or sewing. According to one embodiment, electrode base housing 150 may be configured to be coupled to a "loop" (e.g., Velcro®) fastening layer 256, disposed in a groove in the internal perimeter of housing 150. According to one embodiment, in order to releasably couple electrode pad 56a to electrode base housing 150, the user may position electrode pad 56a inside housing 150 and thereby hook layer 252 of electrode pad 56a and loop layer 256 may be reversibly coupled, ensuring contact between conducting layer 154 of electrode base housing 150 and conducting layer 258 of electrode pad 56a.

Conductive layer 258 may be configured to include a layer of conductive paint that may preferably be printed on its bottom surface configured to face conductive layer 154 of electrode base housing 150. The conductive paint layer may improve the current distribution across conducting layer 258 and liquid absorbing layer 254 and thereby may improve current distribution at the contacting skin surface.

Electrode pad 56a may be configured to include a conducting "male" connector, such as a "male" snap connector, that may be physically and electrically coupled to electrode pad 56a and can be reversibly connected physically and mechanically to a corresponding "female" snap connector in electrode base housing 150, which may be electrically coupled to the headset electrical circuit.

Figure 18A:
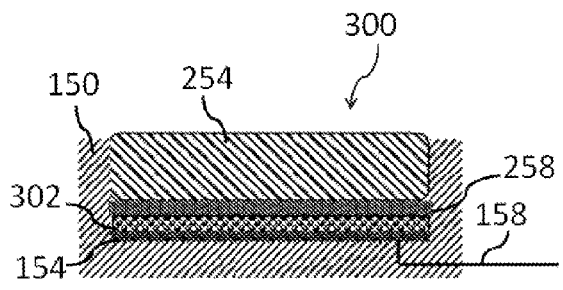
Figure 18B:
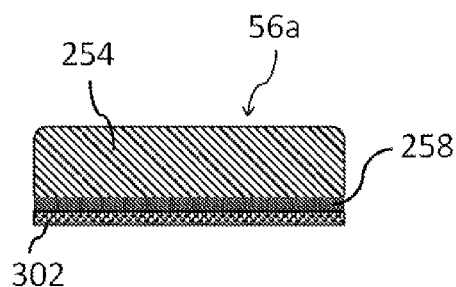

With reference now to FIGS. 18A and 18B, electrode pad 56a may include three layers: a liquid absorbing layer 254, a flexible conductive layer 258, preferably made of a flexible carbon layer and an adhesive hydrogel layer 302. Liquid absorbing layer 254 and flexible conductive layer 258 can be attached by various manufacturing process such as heat welding, RF welding, ultrasonic welding, gluing or sewing. Adhesive hydrogel layer 302 may be adhered to flexible conductive layer 258 by the adhesive properties of the hydrogel layer. According to one embodiment, in order to releasably couple electrode pad 56a to electrode base housing 150, the user may position electrode pad 56a inside housing 150 and thereby the adhesive hydrogel layer 302 of electrode pad 56a and conductive layer 154 may be reversibly coupled, ensuring stable physical and electrical coupling of electrode base housing 150 and electrode pad 56a.

Figure 19A:
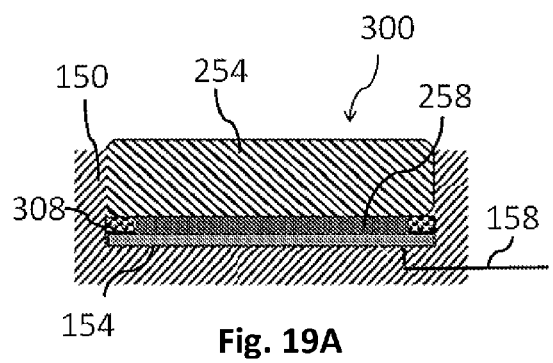
Figure 19B:
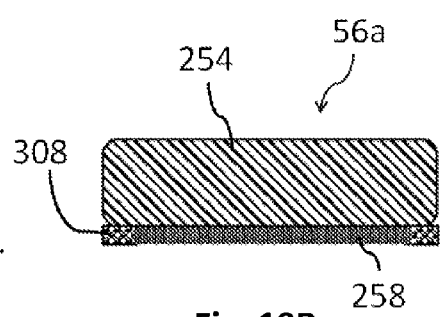

With reference now to FIGS. 19A and 19B, electrode pad 56a may be configured to include a liquid absorbing layer 254, a flexible conductive layer 258, (e.g., made of a flexible carbon layer), and a double adhesive layer 308, coupled to at least portion of the bottom perimeter of electrode pad 56a which is configured to face conductive layer 154 of housing 150. Liquid absorbing layer 254 and flexible conductive layer 258 can be attached by various manufacturing process such as heat welding, RF welding, ultrasonic welding, gluing or sewing. Double side adhesive layer 308 may be adhered to flexible conductive layer 258 by its adhesive properties. According to one embodiment, in order to releasably couple electrode pad 56a to electrode base housing 150, the user may position electrode pad 56a inside housing 150 and thereby the double side adhesive layer 308 of electrode pad 56a and housing 150 may be reversibly coupled, ensuring stable physical and electrical coupling of electrode base housing 150 and electrode pad 56a.

Figure 20A:
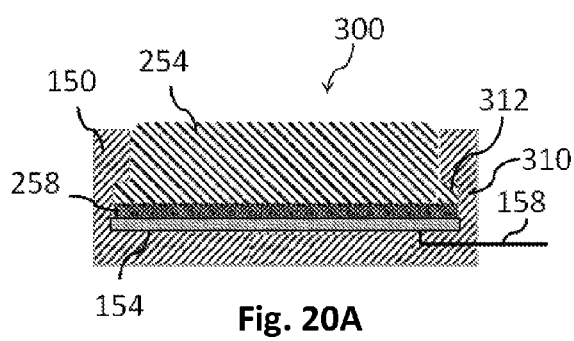
Figure 20B:
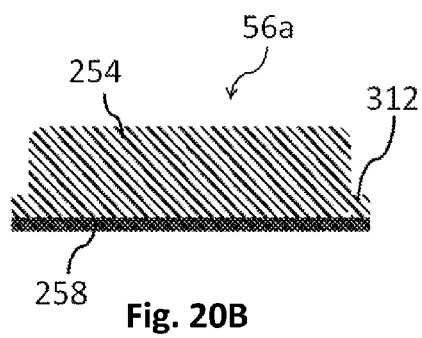

With reference now to FIGS. 20A and 20B, electrode pad 56a may be configured to include a liquid absorbing layer 254 and a flexible conductive layer 258, preferably made of flexible carbon. Liquid absorbing layer 254 and flexible conductive layer 258 can be attached by various manufacturing process such as heat welding, RF welding, ultrasonic welding, gluing or sewing. Electrode pad 56a may include a peripheral edge 312 that is thinner than the central area of liquid absorbing layer 254. The thinner edge 312 can be made by certain manufacturing process such as ultrasonic welding, RF welding or heat compression. The user can reversibly couple electrode pad 56a to electrode base housing 150 by pressing electrode pad 65a into housing 150, until the thinner edge 312 is "snapped" into the corresponding groove 310 in housing 150. In this position, conductive layer 258 of electrode pad 56a and conductive layer 154 of electrode base housing 150 are attached and therefore when the headset is donned, electrical current can be transferred from conductive layer 154 to conductive layer 258 and to liquid absorbing layer 254 and then to the skin surface.

Figure 21:
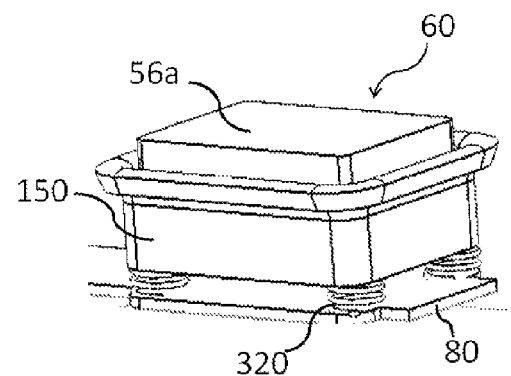
FIG. 21 provides a perspective view of a spring-mounted electrode base housing containing an electrode pad.

FIG. 21 illustrates a perspective view of an electrode base 60. According to certain features of the described preferred embodiments electrode base 60 may be configured to include at least one spring mechanism 320 which may be configured to be physically coupled at one side to flexible member 80 and at its other side to electrode base housing 150. Spring mechanism 320 may be configured to provide "self-adjustment" capabilities for electrode base housing 150, so that when the headset is donned, spring mechanism 320 is compressed or expanded according to the force applied on electrode base housing 150 by the headset and the counter force applied by the head. In certain embodiments spring mechanism 320 may include an elastic mechanism or a sponge instead or in addition to a metal or plastic spring.

Figure 21A:
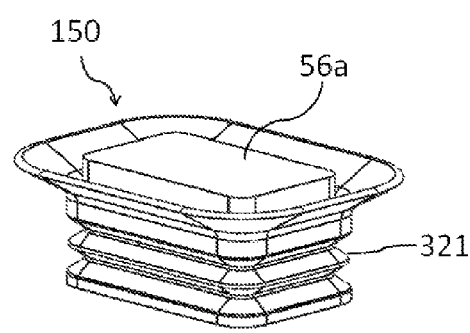
FIGS. 21A and 21B provide perspective and cross-sectional views, respectively of an electrode pad and bellows-type electrode base housing, according to an embodiment of the present invention.
Figure 21B:
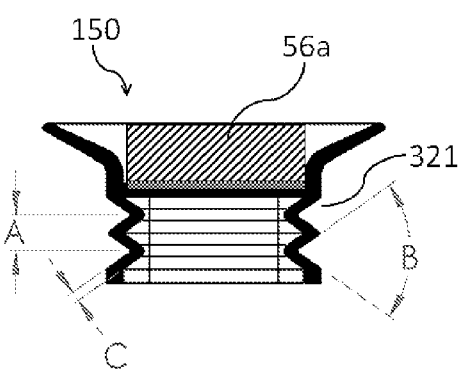

FIGS. 21A and 21B provide perspective and cross-sectional views, respectively, of an electrode pad 56a and a bellows-type electrode base housing 150, according to an embodiment of the present invention. Electrode base housing 150 may be configured to include a flexible bellows carrier 321 that may be configured to be physically coupled to, or be extended from, the bottom of electrode base housing 150. Flexible bellows carrier 321 may be configured to provide "self-adjustment" capabilities for electrode base housing 150, such that when the headset is donned, bellows carrier 321 is compressed or expanded according to the force applied on electrode base housing 150 by the headset and the counter force applied by the head.

With reference to FIG. 21B, flexible bellows carrier 321 may be configured to have the following dimensions:
A—The height of each crease of the bellows. A may be within a range of 1 mm-8 mm, 2 mm-6 mm, or 2 mm-4 mm;
B—The angle of each crease of the bellows. B may be within a range of 40°-90°, 50°-80°, or 60°-80°;
C—The thickness of the wall of the bellows. C may be within a range of 0.3 mm-3 mm, 0.4 mm-2 mm, or 0.5 mm-1.5 mm.

Figure 21C:
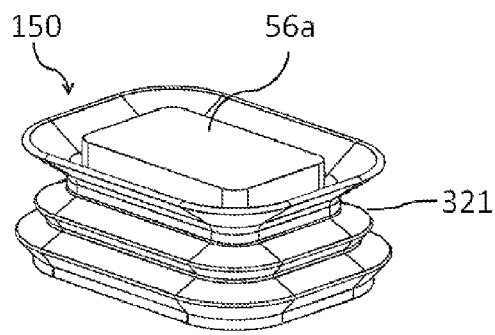
FIGS. 21C and 21D provide perspective and cross-sectional views, respectively of an electrode pad and collapsing electrode base housing, according to an embodiment of the present invention.
Figure 21D:
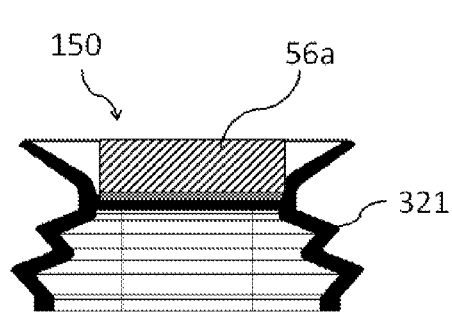

FIGS. 21C and 21D provide perspective and cross-sectional views, respectively of an electrode pad 56a and electrode base housing 150 having a conical shaped bellows carrier 321, according to embodiments of the present invention. Conical shaped flexible bellows carrier 321 may be configured to be physically coupled to, or extended from, the bottom of electrode base housing 150. Bellows carrier 321 may be configured to provide "self-adjustment" capabilities for electrode base housing 150, such that when the headset is donned, bellows carrier 321 may be compressed or expanded according to the force applied on electrode base housing 150 by the headset and the counter force applied by the head. Bellows carrier 321 may be configured to reversibly and repeatedly collapse to less than 50%, less than 40%, less than 30%, or less than 20% of its initial, relaxed height. This may enable appreciably improved alignment of the headset and electrode pad 56a against the head.

Figure 22:
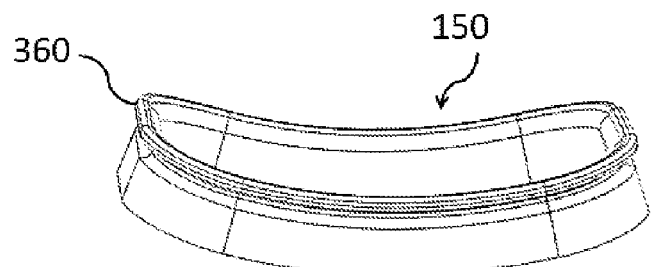
FIG. 22 is a perspective view of an inventive electrode base housing having a circumferential sealing rim.

FIG. 22 is a perspective view of electrode base housing 150. According to one embodiment, electrode base housing 150 is configured to include a circumferential sealing rim 360. Stimulation in the presence of hair, such as when attempting to non-invasively stimulate various areas of the head, presents a challenge, since the hair creates a high impedance layer between the superficial electrodes and the skin. Solid adhesive hydrogel is the most common conductive medium used in electrical stimulation electrodes. However, hydrogel may not be particularly suitable for use in the presence of hair, due to poor penetration of the hair layer.

Tap water may be suitable from a penetration standpoint, since it can pass through the hair layers and does not leave residue, and is commonly available. The inventors have found that in order to ensure the required conductivity and substantially even current distribution, a substantial layer of water should be maintained against the scalp during the treatment and dehydration should be prevented, especially during prolonged treatment sessions. Prevention of electrode dehydration may also be required in areas that do not include hair, such as the forehead.

However, in some embodiments, the electrode pad 56a may be pre-soaked with a conductive gel, thus allowing for better conductivity and stimulation and reduced dehydration than those achieved with water. This embodiment is advantageous in that it maintains user-friendliness in that the user need not apply the gel to the pad himself, and in that the gel is mostly contained within the pad, such that excess amounts of gel substantially do not spread over and out of the stimulation area. As mentioned above, the conductive gel may be any commercially available conductive gel suitable for use with electrodes.

Figure 23:
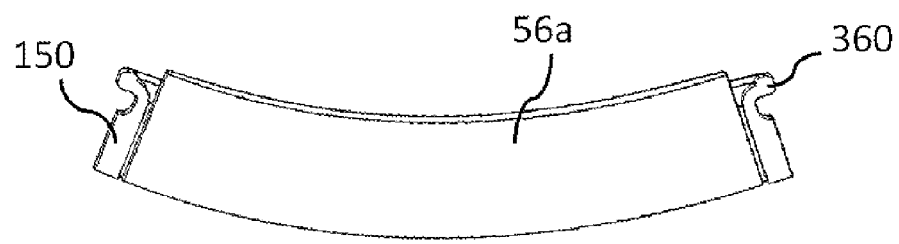
FIG. 23 provides a cross-sectional view of the electrode base housing shown in FIG. 22, the housing having an electrode pad disposed therein.

FIG. 23 provides a cross-sectional view of electrode base housing 150 with electrode pad 56a inserted.

Figure 24:
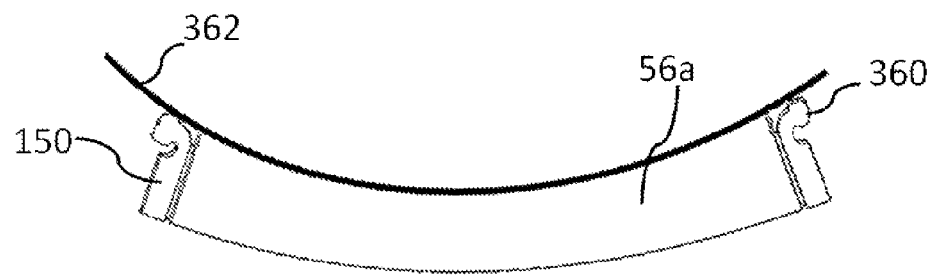
FIG. 24 provides a cross-sectional view of the electrode base housing and electrode pad shown in FIG. 22, the electrode pad being urged against a skin surface.

FIG. 24 is a cross-sectional view of electrode base housing 150 with electrode pad 56a inserted, while urged against a skin surface 362. The housing 150 may be adapted such that a pressure exerted against electrode base 60 (not shown) perpendicularly to the sealing rim 360 and towards a skin surface 362 of a user, urges sealing rim 360 against the skin surface to substantially seal the cavity created between sealing rim 360 and the skin surface 362 of the user and an ambient or external environment.

Sealing rim 360 may be made of flexible material such as TPU or silicon, and may be configured to have a modulus of elasticity that is sufficient to maintain a level of pressure against the scalp that provides the required sealing effect. However, an overly large modulus of elasticity may result in excessive pressure against the scalp. Sealing rim 360 may be sufficiently pliant to be self-aligning to various head contours. Sealing rim 360 may be configured to have a high drag coefficient, in order to assist in stabilizing the electrode in place against the scalp. Also, sealing rim 360 may be configured to prevent dehydration of the wetted pad and the liquid contained within the sealed space and thereby to enable effective and prolonged sessions of stimulation. Sealing rim 360 may be configured to be detachable from the electrode base when the stimulation electrode is placed in areas where sealing is not needed.

The headset may be configured to include sealing rims having various contours, to ensure proper sealing functionality at specific skin surfaces and locations. In order to reach the required sealing effect, sealing rim 360 may be configured to include material that inflates in the presence of liquid such as water.

Electrode base housing 150 with sealing rim 360 may be configured to be used in areas that do not include hair such as the forehead or other areas of the body, for example, in order to prevent electrode pad dehydration.

Figure 25:
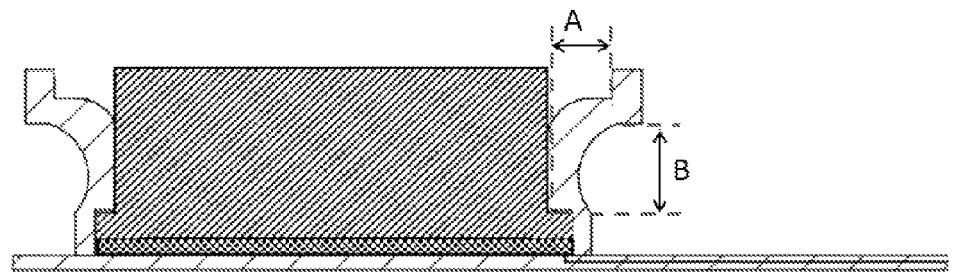
FIG. 25 is a cross-sectional view of an electrode base in which the wall geometry is defined.

Electrode base housing 150 with sealing rim 360 may be configured to include the following dimensions (see FIG. 25):

The inner surface of the flexible circumferential wall of housing 150 has a radial curvature, wherein a radial distance (A) between an inner surface of rim 360 and a most radially inward point of the inner surface of the wall of housing 150, is in the range of 1 to 15 mm, 2 mm to 10 mm, or 2 mm to 7 mm.

The outer surface of the flexible circumferential wall of housing 150 has a radial curvature, wherein the length (B) of the curvature is within a range of 1 mm to 15 mm, 2 mm to 10 mm, or 2 mm to 8 mm.

Figure 25A:
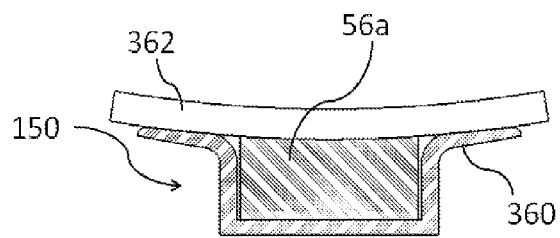
FIG. 25A provides a cross-sectional view of an inventive electrode base housing containing an electrode pad, the electrode pad being urged against a skin surface.

FIG. 25A provides a cross-sectional view of an inventive electrode base housing 150 having a sealing rim 360 and containing an electrode pad 56a, the electrode pad being urged against a skin surface 362. The housing 150 may be adapted such that a pressure exerted against electrode base 60 (not shown) perpendicularly to the sealing rim 360 and towards a skin surface 362 of a user, urges sealing rim 360 against the skin surface to substantially seal the cavity created between sealing rim 360 and the skin surface 362 of the user and an ambient or external environment.

Sealing rim 360 may be made of flexible material such as TPU or silicon, and may be configured to have a modulus of elasticity that is sufficient to maintain a level of pressure against the scalp that provides the required sealing effect. However, an overly large modulus of elasticity may result in excessive pressure against the scalp.

According to certain embodiment the level of hardness of sealing rim 360 may be 20-50 Shore A, more preferably 20-40 Shore A, most preferably 30-40 Shore A.

According to certain embodiment the modulus of elasticity (E) of sealing rim 360 (at 100% strain) is 0.4 MPa-3 MPa, 0.5 MPa-2 MPa, or 0.5 MPa-1.2 MPa.

Sealing rim 360 may be configured to prevent dehydration of the wetted pad and the liquid contained within the sealed space and thereby to enable effective and prolonged sessions of stimulation.

Figure 25B:
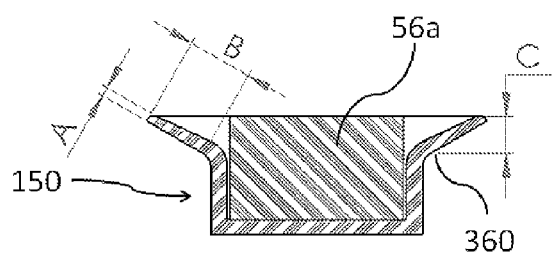
FIG. 25B provides a cross-sectional view of the housing and pad arrangement of FIG. 25A in a relaxed mode, and in which the wall geometry is defined.

FIG. 25B provides a cross-sectional view of the housing 150, sealing rim 360 and pad 56a arrangement of FIG. 25A in a relaxed mode, and in which the wall geometry is defined. Electrode base housing 150 with sealing rim 360 may be configured to have the following dimensions (see FIG. 25B):

Sealing rim wall thickness (A) may be 0.3 mm-3.0 mm, 0.4 mm-1.5 mm, or 0.5 mm-1 mm.

Sealing rim curvature length (B) may be 1 mm-10 mm, 2 mm-8 mm, or 3 mm-6 mm.

Sealing rim curvature height (C) may be 1 mm-10 mm, 2 mm-8 mm, or 2 mm-4 mm.

Figure 25C:
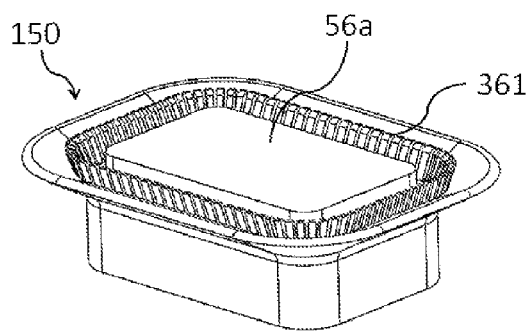
FIG. 25C provides a perspective view of an inventive electrode base housing containing an electrode pad, the housing containing a plurality of closely spaced sealing fingers circumferentially enveloping the electrode pad.

FIG. 25C provides a perspective view of an inventive electrode base housing 150 containing an electrode pad 56a, the housing containing a plurality of closely spaced sealing fingers 361 circumferentially enveloping the electrode pad 56a. Housing 150 may be adapted such that a pressure exerted against electrode base 60 (not shown) perpendicularly to the sealing fingers 361 and towards a skin surface of a user, urges sealing fingers 361 against the skin surface to at least partially seal, or at least substantially seal, the cavity created between sealing fingers 361 and the skin surface of the user and an ambient or external environment.

Sealing fingers 361 may be made of flexible material such as TPU or silicon, and may be configured to have a modulus of elasticity that is sufficient to maintain a level of pressure against the scalp that provides the required sealing effect.

According to certain embodiment, sealing "fingers" 361 are configured to self-align to various surface/skin contours. The fluid surface tension prevents it from flowing between fingers 361 and thereby the fluid is kept around pad 56a.

Figure 25D:
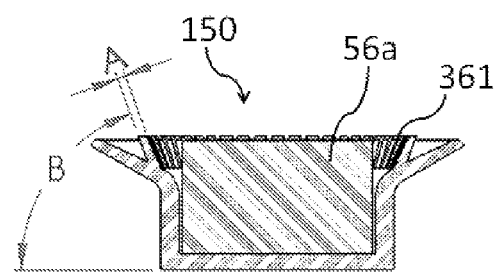
FIG. 25D provides a cross-sectional view of the housing and pad arrangement of FIG. 25C.

FIG. 25D provides a cross-sectional view of the arrangement of FIG. 25C.

Figure 25E:
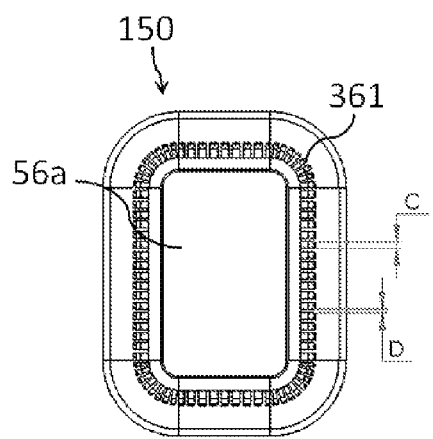
FIG. 25E provides a top view of the housing and pad arrangement of FIG. 25C.

FIG. 25E provides a top view of the arrangement of FIG. 25C. Electrode base housing 150 with sealing fingers 361 may be configured to include the following dimensions (see FIGS. 25D and 25E):

The thickness (A) of a sealing finger 361 is preferably 0.3 mm-1.5 mm, more preferably 0.4 mm-1.2 mm, most preferably 0.5 mm-1 mm.

The angle (B) of a sealing finger 361 is preferably 20°-90°, more preferably 40°-80°, most preferably 60°-80°.

The width (C) of a sealing finger 361 is preferably 0.3 mm-3 mm, more preferably 0.4 mm-2.5 mm, most preferably 0.5 mm-1.5 mm.

The gap (D) between sealing fingers 361 is preferably 0.1 mm-1.5 mm, more preferably 0.2 mm-0.1 mm, most preferably 0.2 mm-0.8 mm.

Figure 25F:
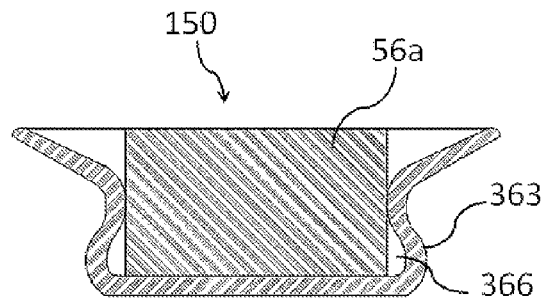
FIG. 25F provides a cross-sectional view of an inventive housing and pad arrangement in which the housing wall curvature is adapted to trap excess fluid.

FIG. 25F provides a cross-sectional view of an inventive housing 150 and pad 56a arrangement in which a wall curvature 363 of housing 150 is adapted to trap and store excess fluid in the cavity 366 created between the inner wall curvature and pad 56a. When the headset is donned, pad 56a is urged against the head and may release some of its excess fluid into cavity 366. The fluid contained in cavity 366 may later be reabsorbed by pad 56a and released toward the skin surface.

Figure 25H:
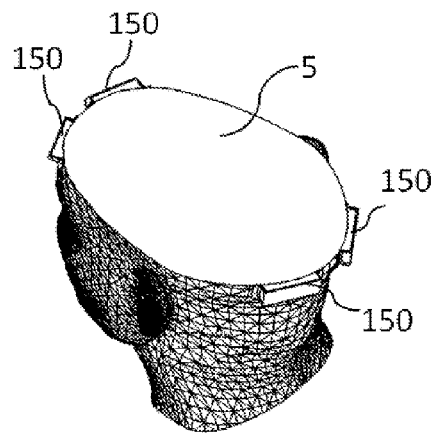
FIG. 25G provides a schematic perspective cross-sectional view of one embodiment of the inventive headset, positioned on a head of a user, and FIG. 25H provides magnified views of the electrode base housings urged against the head.
Figure 25G:
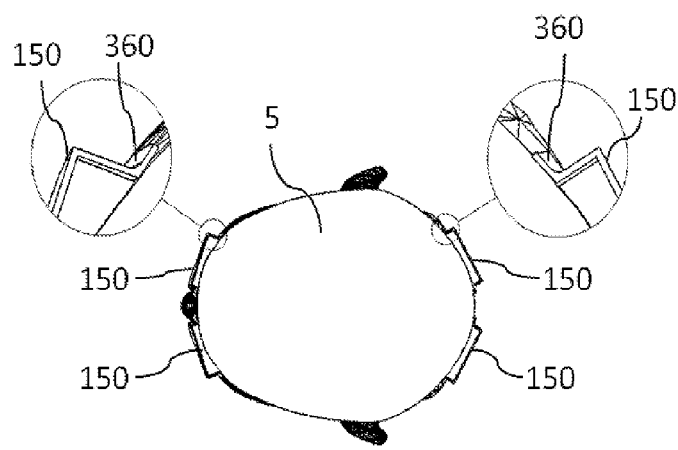

FIG. 25G provides a schematic perspective cross-sectional view of one embodiment of the inventive electrode base housings 150 positioned on a head 5 of a user and urged against the head, and FIG. 25H provides magnified views of the electrode base housings 150 and sealing rims 360 urged against head 5.

Figure 26:
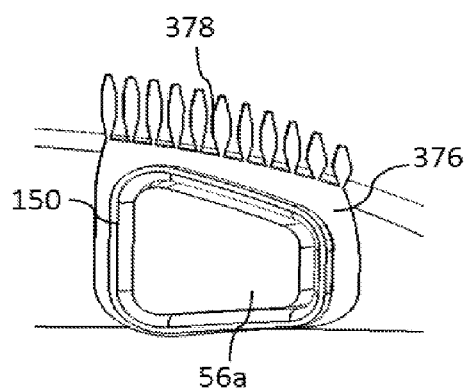
FIG. 26 is a perspective view of a flexible, comb-like member disposed above an electrode base housing, according to embodiments of the invention.

FIG. 26 is a perspective view of a flexible, comb-like ("hair clearing") member 376 disposed above an electrode base housing, according to embodiments of the invention. Member 376 may be configured to be physically coupled to the headset above electrode base housing 150, and may be configured to include several elongated rigid and preferably semi-rigid members or teeth 378.

Figure 27:
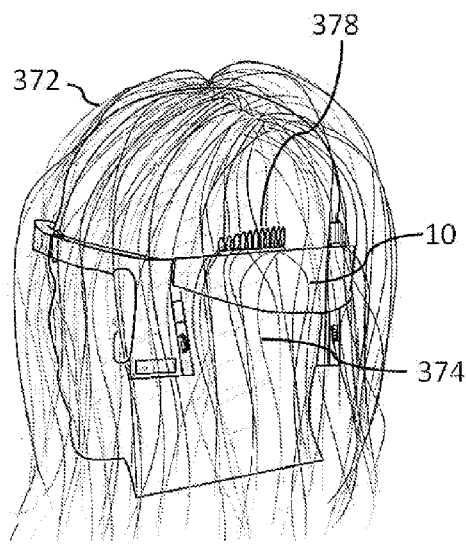
FIG. 27 is a perspective rear view of a donned headset in which the flexible, comb-like member of FIG. 26 protrudes above the circumferential band of the headset.

FIG. 27 is a perspective rear view of a donned headset in which the flexible, comb-like member 376 protrudes above the circumferential band of headset 10. While the user dons headset 10 on his head 372, elongated members 378 may be configured to jut above the electrodes at areas that include hair, such as the back or sides of the head. Comb-like member 376 may be configured to enable simple donning of headset 10 while ensuring temporarily pushing away and clearing of hair layers under the electrodes so that only minimal amount of hair will remain between the electrodes and the skin. Flexible, comb-like member 376 may be configured to function like a comb, separating layers of hair 374 from the scalp while headset 10 with its electrodes is pushed upward by the user into an operating position on head 372, thereby ensuring the required electrical conductivity between the electrodes and the skin.

According to another features of the described preferred embodiments, member 376 may be configured to be detachable from headset 10 in order to enable its removal by the user, for example, in the case that the user has short hair.

The invented headset is configured to stimulate various areas of the head by electrodes in various shapes and sizes. The headset may include electrodes configured to stimulate the forehead region.

Figure 28:
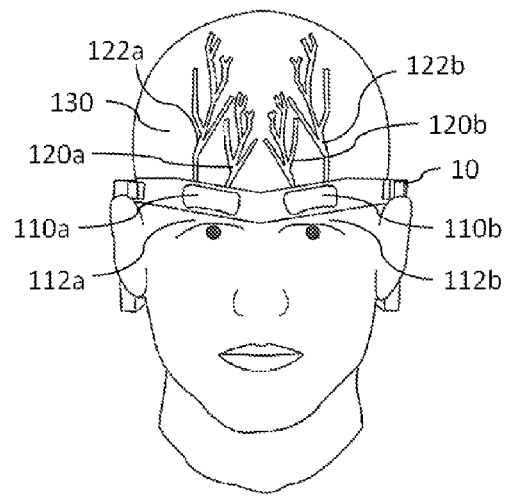
FIG. 28 is a perspective anterior view of a donned headset, the headset configured, and the front electrodes adapted and positioned to stimulate specific nerve branches in the forehead region, according to embodiments of the invention.

FIG. 28 is a perspective anterior view of a donned headset 10, the headset configured, and the front electrodes 110*a* and 110*b* adapted and positioned, to stimulate specific nerve branches in the forehead region. These specific nerve branches include the supratrochlear 120*a*, 120*b* and supraorbital 122*a*, 122*b* nerves, both of which are superficial branches of the trigeminal nerve. Electrodes 122*a* and 122*b* may be configured to have a narrow elongated contour and to be at least partially aligned with the contour of the eyebrows 112*a* and 112*b* in order to achieve the desired nerve depolarization with minimal stimulation intensity and sufficient level of sensory comfort. Electrodes 110*a* and 110*b* may be configured to have a minimal size and a particular shape, in order to minimize unpleasant sensation that may be elicited when pain nerve fibers disposed on the periosteum of the skull bone are activated. Electrodes 110*a* and 110*b* may be also configured to ensure proper stimulation of the target nerves despite the wide range of morphological variables in the target population. An additional consideration that may influence the dimensions of the electrode and specifically its length, is an expected deviation that may occur in the rotational placement of headset 10, when donned by the user. Therefore, the electrodes may preferably be configured to have sufficient length to ensure placement of at least part of the electrode above the target nerves, even when such rotational deviation occurs.

Figure 29:
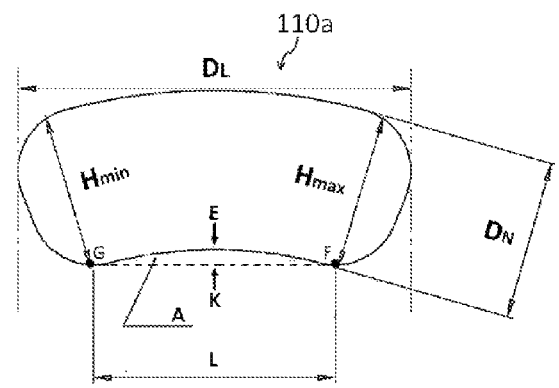
FIG. 29 provides the dimensions of an inventive electrode configured to selectively stimulate nerve branches in the supraorbital region.

FIG. 29 is an illustration of an embodiment of electrode 110*a* which electrode may be configured for stimulation of the supraorbital region. Electrode 110*a* may include a biocompatible conducting material configured to face the skin surface, and may be configured to include an electrode backing attached to a conductive contact surface. The backing may contain at least one conductive material or element that may be electrically coupled with the conductive contact surface.

Electrode 110*a* may be configured to have a conductive contact surface with the following dimensions:
(i) a long dimension ($D_L$) having a length of 20 mm to 55 mm, 25 to 50 mm, or 30 to 45 mm.
(ii) a narrow dimension ($D_N$) having a length of 10 mm to 30 mm, 10 to 25, or 12 to 20 mm.

Concave contour E has a concavity defined by boundary points G and F, which points are disposed at opposite ends of the concavity.

Typically, A/L is at least 0.5 mm,
A being an area bounded by dotted line K and the concavity; L being a length of line K (between boundary points G and F), (L) being at least 10 mm, wherein a line disposed between a first point on the concave contour and a second point on the perimeter of electrode 110*a*, on a side opposite to concave contour E, and aligned in perpendicular fashion with respect to contour E at the first point, has a length H, and wherein, over an entirety of the concave contour, $$H_{max}/H_{min} \leq 2.5$$

$H_{max}$ being a maximum value of H over this entirety; and $H_{min}$ being a minimum value of H over this entirety.

The distance between two electrodes configured to stimulate the supraorbital region may be in a range of 5-45 mm, 8-35 mm, or 8-25 mm. Additional electrodes may be located on the headset in order to stimulate other nerves, for example, the zygomaticotemporal nerve or the auriculotemporal nerve. The headset may also include electrodes that are configured to stimulate the occiput region.

Figure 30:
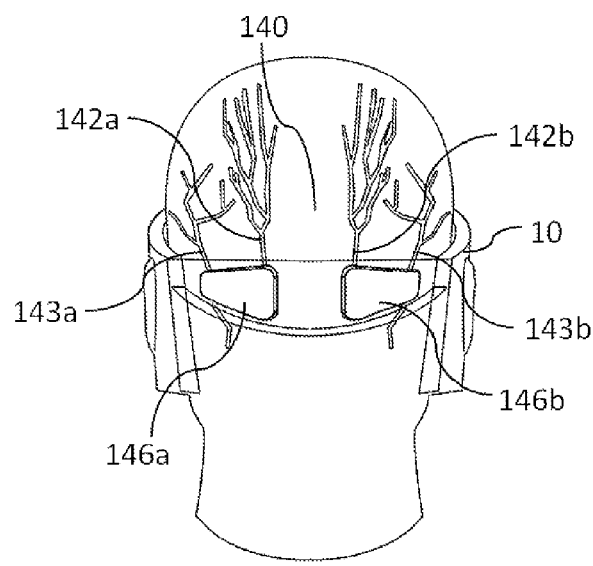
FIG. 30 is a perspective rear view of a donned headset, the headset configured, and the rear electrodes adapted and positioned to stimulate specific nerve branches in the occipital nerve region, according to embodiments of the invention.

FIG. 30 provides an embodiment in which electrodes 146*a* and 146*b* are configured to be located at the rear aspect (facing the occiput) of headset 10 in order to stimulate nerves at the occiput region 140, such as the left side greater occipital nerve 142*a* and the right side greater occipital nerve 142*b*. Additional electrodes may be located in the headset and configured to stimulate other nerves in the head region, such as left and right lesser occipital nerves 143*a* and 143*b*.

In order to stimulate the branches 142*a* and 142*b* of the greater occipital nerve, the electrodes may be configured to be positioned above the nerve branches at approximately the level of the occipital protuberance, where the branches of the greater occipital nerve become superficial after piercing the trapezius fascia. Stimulation below this anatomical area may cause disadvantageous contraction of the upper neck muscles while stimulation at a higher area may cause disadvantageous contraction of the scapularis muscle and may cause painful sensation due to proximity to the nociceptive nerve fibers of the skull periosteum. It is therefore important to ensure that stimulation performed with accurate placement of the electrodes and with electrodes that have appropriate dimensions that ensure effective stimulation with high level of sensory comfort and without overflow of the stimulation to nearby muscles. In some embodiments, the dimensions of electrodes 146*a* and 146*b* are preferably in the range of 20-50 mm in length and 8-40 mm in height; electrodes 146*a* and 146*b* may be disposed at a distance of 5-35 mm from the occiput midline. More typically, electrodes 146*a* and 146*b* have a length within a range of 25-45 mm and a height within a range of 10-25 mm; electrodes 146*a* and 146*b* may be disposed at a distance of 8-25 mm from the occiput midline.

Figure 31:
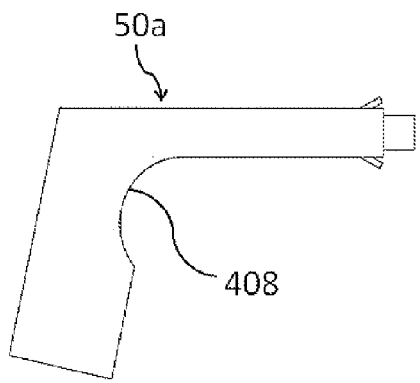
FIG. 31 provides a side perspective view of a bilateral member of an inventive headset, according to one embodiment of the invention.

FIG. 31 illustrates a side perspective view of bilateral member 50*a* which, according to one embodiment, is part of the inventive headset. According to certain features of the described preferred embodiments, member 50*a* is configured to be rigid and preferably semi-rigid, having a curved portion 408 adapted to align behind and above the ear.

Figure 32:
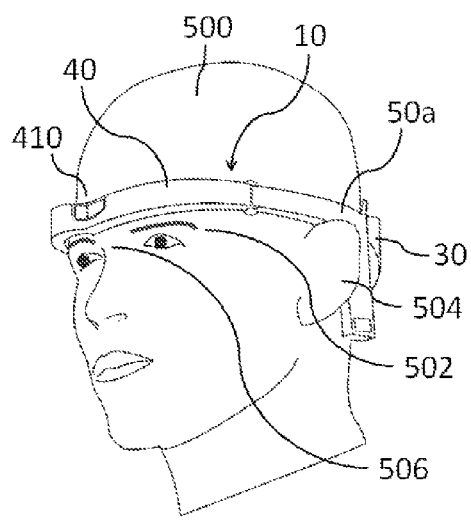
FIG. 32 is a perspective view of a donned, inventive headset.

FIG. 32 illustrates a perspective view of headset 10 on head 500. Headset 10 may be configured to enable accurate placement on the head in a way that may be both repeatable and intuitive for a user without clinical expertise. Precise electrode placement over the target peripheral nerves and brain areas is essential in order to achieve the desired therapeutic benefits. When stimulating the head region, accurate electrode placement is especially important, since even slight deviation in the electrode position may elicit unpleasant sensation and even pain, due to stimulation over the periosteum of the skull bone, or may cause unwanted motor contraction of muscles such as the frontalis, temporalis, scapularis or the upper neck muscles.

Bilateral rigid and preferably semi-rigid member 50*a* may be configured to enable the user to position headset 10 on his head 500 in a substantially accurate and repeatable manner. When curved bilateral member 50*a* is positioned behind and above both ears, both the circumferential (rotational) and longitudinal placement of headset 10 are determined with respect to head 500.

Headset 10 may be configured to include a recess 410 at its anterior portion, configured to be aligned with the glabella midline and above a nose bridge 506. In order to ensure proper circumferential (rotational) and longitudinal placement of headset 10 with respect to head 500 without the need to use a mirror, the user may position his thumb on nose bridge 506 and one of his fingers (of the same hand) on recess 410, to ensure that headset 10 is accurately positioned.

The contour of frontal elastic member 40 of headset 10 may be configured to align with the anatomical lines of eyebrows 502 and an upper area of nose bridge 506, such that when it is aligned by the user above the eyebrows, the headset rotational and longitudinal orientation is determined.

In order to suit each particular user, the rotational position of the bilateral semi-rigid members 50*a*, relative to headset 10, may be individually adjusted; semi-rigid members 50*a* of different size and shape may be selected in order to optimally adjust the orientation of headset 10; frontal elastic member 40 of various contours may be selected in order to adjust the anterior longitudinal orientation of the headset; and the position of recess 410 may be adjusted or headset 10 and its integrated electrodes may be configured for a non-symmetrical alignment, as necessary.

Posterior elastic member 30 of headset 10 may be configured to have a concave shape that may be aligned above the occipital protrusion and the nuchal line, thereby the longitudinal placement of headset 10, and more specifically, the longitudinal placement of posterior elastic member, may be determined.

Figure 33:
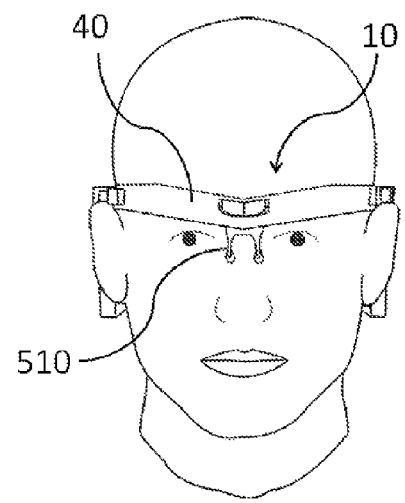
FIG. 33 is a perspective anterior view of a donned, inventive headset having a nose bridge support member.

FIG. 33 is a perspective anterior view of headset 10 with a "nose bridge" member 510. "Nose bridge" member 510 may be configured to be located in the central area of elastic member 40. "Nose bridge" member 510 may be rigid or semi-rigid, and may have two elongated portions adapted to be aligned at both sides of the upper part of the nose and the nose bridge. Positioning the "nose bridge" member over the nose may allow the user to determine headset 10 rotational and longitudinal placement.

The "nose bridge" member 510 may also be configured to further support member 40 against gravity. "Nose bridge" member 510 may be configured to be detachable from headset 10. A "nose bridge" member 510 of various sizes and shapes may be selected for individual users. "Nose bridge" member 510 may be configured to be manually adjusted by the user for optimal adjustment to the nose of the user.

Figure 34:
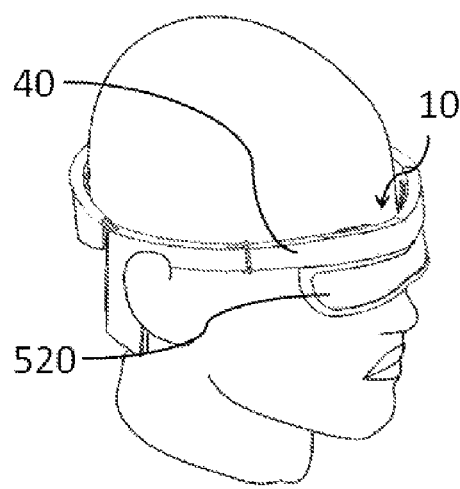
FIG. 34 is a perspective view of a donned, inventive headset having associated eyeglasses.

FIG. 34 is a perspective view of headset 10 having eyeglasses 520. Eyeglasses 520 may be adapted to be coupled to frontal elastic member 40. In some embodiments, eyeglasses 520 may be configured to:

be reversibly and repeatedly detachable from headset 10;
include various lenses such as optical lenses for improved eyesight, sunglasses, or non-optical transparent lenses;
include highly dark lenses that may be used to block external light, for example, in order to assist during migraine attack or for relaxation.

Figure 35:
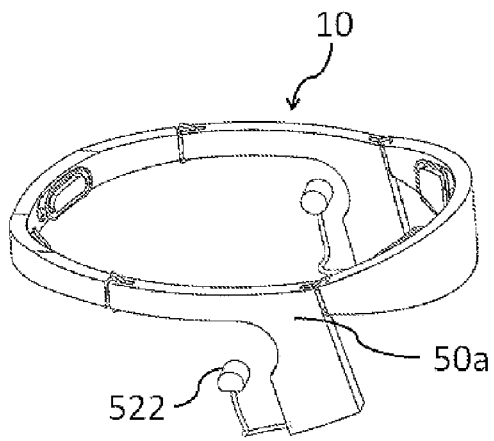
FIG. 35 is a perspective view of an inventive headset having associated earphones.

FIG. 35 is a perspective view illustration of headset 10 having earphones such as bilateral earphones 522. In some embodiments, bilateral earphones 522 may be configured to be electrically connected to an at least semi-rigid bilateral member 50*a*.

In some embodiments, earphones 522 and bilateral member 50*a* may be configured such that earphones 522 are reversibly and repeatedly detachable from bilateral member 50*a*.

In some embodiments, bilateral member 50 may be adapted to include an internal space and an opening that may be served for storage of earphones 522 when earphones 522 are not in use. Bilateral member 50 may include a mechanism that pulls earphones 522 into a storage space within bilateral member 50*a*, when earphones 522 are not in use.

Figure 36:
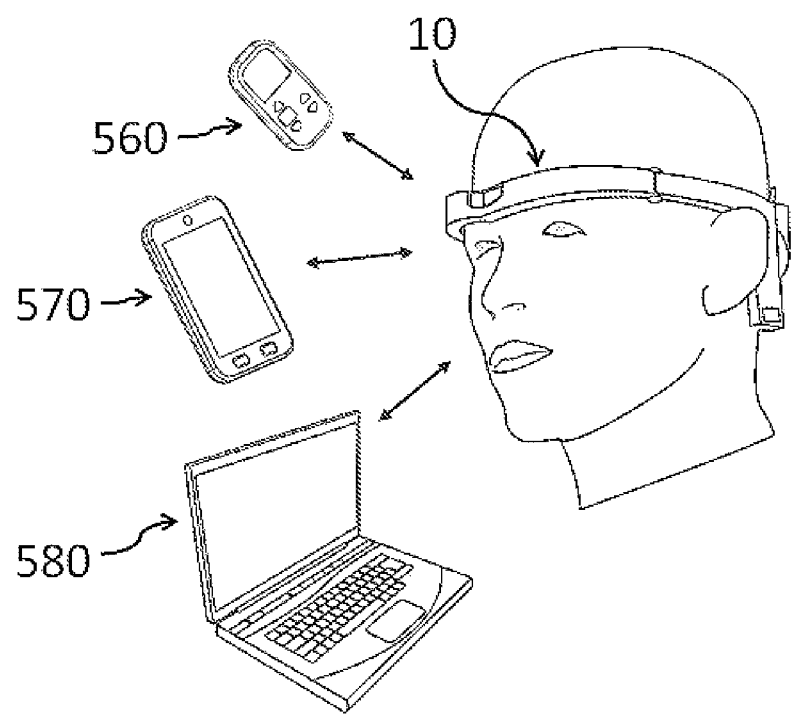
FIG. 36 provides a perspective view of a donned, inventive headset adapted to communicate with a remote control unit, mobile phone, and computer

FIG. 36 illustrates a perspective view of headset 10 along with a remote control or remote control handset 560, a mobile phone 570 and a laptop/PC 580.

In some embodiments, headset 10 may be configured to communicate wirelessly with remote control 560. Remote control 560 may be used by the user to send commands to headset 10, such as stimulation initiation or cessation commands, or commands to increase or decrease the stimulation intensity. Remote control 560 may also present various visual and audio indications for the user regarding the status of headset 10.

Headset 10 may be configured to wirelessly communicate with a mobile phone 570. The mobile phone interface may be used to present various data sent wirelessly by headset 10, for example, visual and audio indications regarding the status of headset 10 and usage logs.

Headset 10 may be configured to wirelessly communicate with laptop/PC 580. The mobile phone interface may be used to present various data sent wirelessly by headset 10, such as visual and audio indications regarding the status of headset 10 and usage logs.

Communication between headset 10 and remote control 560, mobile phone 570 and laptop 580 may be performed in various ways, known to those of ordinary skill in the art, for example by Bluetooth communication.

As used herein in the specification and in the claims section that follows, the term "monolithic" means structurally behaving as a single, at least semi-rigid whole.

As used herein in the specification and in the claims section that follows, the term "monolithically donnable", with respect to a headset, headset frame, or the like, refers to a structure enabling the donning of the headset, headset frame, or the like as a single, at least semi-rigid whole.

As used herein in the specification and in the claims section that follows, the term "operational mode", or the like, with respect to a headset or headset component, refers to a headset or headset component that is fitted onto the head of the user, in a suitable rotational and longitudinal disposition, with electrical stimulation being applied.

As used herein in the specification and in the claims section that follows, the term "donned mode", "donned", or the like, with respect to a headset or headset component, refers to a headset or headset component that is fitted onto the head of the user, in a suitable rotational and longitudinal disposition, with electrical stimulation being applied.

As used herein in the specification and in the claims section that follows, the term "integral" refers to a structure behaving as a single, whole structure. The term may be applied in particular to flexible structures such as an electrode pad.

As used herein in the specification and in the claims section that follows, the term "liquid" refers to a liquid such as water, saline, or a conductive gel.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. Similarly, the content of a claim depending from one or more particular claims may generally depend from the other, unspecified claims, or be combined with the content thereof, absent any specific, manifest incompatibility therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A headset for use in delivering electrical stimulation to a skin surface of a head of a user, the headset comprising:
    (a) a circumferential headset body, said body having a monolithic frame adapted to circumferentially fit around the head of the user, said body housing an electric circuit adapted to be connected to a power source; said headset body including an elastic arrangement, disposed on at least a portion of a circumference of said headset body; said elastic arrangement adapted to be tensioned along said circumference;
    (b) at least one electrode base, mechanically and at least semi-rigidly connected to said headset body, and electrically associated with said electric circuit, said electrode base adapted to receive at least one electrode pad, and having:
        (i) a housing including a floor, and a flexible circumferential member surrounding said floor, and having a flexible circumferential wall extending generally above a perimeter of said floor, said wall ending in a circumferential rim; said floor and said flexible circumferential member forming a cavity adapted to receive an electrically conductive electrode pad; and
        (ii) an electrically conductive material, disposed at least partially above, or within, said floor; said conductive layer adapted to be electrically associated to an electrical circuit, by means of an electrical conductor, and, when said pad is inserted, to electrically communicate with said electrode pad;
    said rim and said flexible circumferential wall adapted such that a pressure exerted against said electrode base, generally perpendicular to said rim, and towards a skin surface of a user, urges said rim against said skin surface, to substantially fluidly seal between said cavity and an ambient or external environment;
    said headset body and said base adapted to orient an electrical stimulation surface of said pad towards the skin surface, during donning by the user;
    said elastic arrangement adapted such that, during said donning, said elastic arrangement radially urges said electrode base towards the skin surface such that said electrode pad makes physical and electrical contact with the skin surface;
    said elastic arrangement and said electrode base adapted such that for various degrees of tensioning of said elastic arrangement, a circumferential position of said electrode base, with respect to said frame, is fixed in a specific predetermined position.

2. The headset of claim 1, said circumferential headset body having a front section adapted to fit around a front portion of the head, said at least one of said at least one electrode base being a front electrode base disposed on said front portion.

3. The headset of claim 1, said frame including at least semi-rigid side components, bi-laterally disposed on said frame, and forming side portions of said circumference of said headset body.

4. The headset of claim 1, said frame including at least a first bi-lateral size adjustment mechanism adapted to fixedly adjust said circumference of said headset body.

5. The headset of claim 1, said headset body adapted to juxtapose a contact surface of an electrical device opposite or against the skin surface, said elastic arrangement adapted to radially urge said electrical device towards said skin surface such that a contact surface of said electrical device makes physical contact with said skin surface; said elastic arrangement adapted such that for various degrees of tensioning of said elastic arrangement, a circumferential position of said electrical device is fixed in a particular device position.

6. The headset of claim 5, said electrical device including a sensor adapted to sense a body parameter associated with the head of the user.

7. The headset of claim 1, said at least one electrode pad including:
    (a) a liquid-absorbent layer having a biocompatible, conductive contact surface, said contact surface adapted to be juxtaposed against the skin surface;
    (b) an electrically conductive layer having a broad first face juxtaposed against, or attached to, said liquid-absorbent layer, said conductive layer containing at least one electrically conductive material or element, said conductive layer adapted to transfer an electrical current from a broad second face, distal to said first face, to said liquid-absorbent layer, via said first face.

8. The headset of claim 7, said liquid-absorbent layer including at least one material selected from the group consisting of a non-woven fabric, felt or sponge.

9. A headset for use in delivering electrical stimulation to a skin surface of a head of a user, the headset comprising:
    (a) a circumferential headset body, said body having a monolithic frame adapted to circumferentially fit around the head of the user, said body housing an electric circuit adapted to be connected to a power source; said headset body including an elastic arrangement, disposed on at least a portion of a circumference of said headset body;
    (b) at least one electrode base, mechanically and at least semi-rigidly connected to said headset body, and electrically associated with said electric circuit, said electrode base adapted to receive at least one electrode pad;
    said headset body and said base adapted to orient an electrical stimulation surface of said pad towards the skin surface, during donning by the user;

said elastic arrangement adapted such that, during said donning, said elastic arrangement radially urges said electrode base towards the skin surface such that said electrode pad makes physical and electrical contact with the skin surface;

said elastic arrangement and said electrode base adapted such that for various degrees of tensioning of said elastic arrangement, a circumferential position of said electrode base, with respect to said frame, is fixed in a specific predetermined position;

said circumferential headset body having a front section adapted to fit around a front portion of the head, said at least one of said at least one electrode base being a front electrode base disposed on said front portion, said front section being a front mechanical element that is physically distinct from said circumferential headset body.

10. The headset of claim 9, said front mechanical element spanning at most 40% of a circumference of said circumferential headset body.

11. The headset of claim 9, said frame including a positioning system for angular and longitudinal positioning of said headset body, said positioning system including at least one at least semi-rigid side component, said side component having:
   (i) a first, elongated element, forming a portion of said circumference, and adapted to fit above an ear of the user, to determine said longitudinal positioning, and
   (ii) a second element disposed generally perpendicular to said elongated element, and adapted to fit behind said ear, to determine said angular positioning of said headset body.

12. The headset of claim 9, said frame including at least semi-rigid side components, bi-laterally disposed on said frame, and forming side portions of said circumference of said headset body.

13. The headset of claim 9, said frame including at least a first bi-lateral size adjustment mechanism adapted to fixedly adjust said circumference of said headset body.

14. The headset of claim 9, said headset body adapted to juxtapose a contact surface of an electrical device opposite or against the skin surface, said elastic arrangement adapted to radially urge said electrical device towards said skin surface such that a contact surface of said electrical device makes physical contact with said skin surface; said elastic arrangement adapted such that for various degrees of tensioning of said elastic arrangement, a circumferential position of said electrical device is fixed in a particular device position.

15. The headset of claim 14, said electrical device including a sensor adapted to sense a body parameter associated with the head of the user.

16. The headset of claim 9, said at least one electrode pad including:
   (a) a liquid-absorbent layer having a biocompatible, conductive contact surface, said contact surface adapted to be juxtaposed against the skin surface;
   (b) an electrically conductive layer having a broad first face juxtaposed against, or attached to, said liquid-absorbent layer, said conductive layer containing at least one electrically conductive material or element, said conductive layer adapted to transfer an electrical current from a broad second face, distal to said first face, to said liquid-absorbent layer, via said first face.

17. A headset for use in delivering electrical stimulation to a skin surface of a head of a user, the headset comprising:
   (a) a circumferential headset body, said body having a monolithic frame adapted to circumferentially fit around the head of the user, said body housing an electric circuit adapted to be connected to a power source; said headset body including an elastic arrangement, disposed on at least a portion of a circumference of said headset body;
   (b) at least one electrode base, mechanically and at least semi-rigidly connected to said headset body, and electrically associated with said electric circuit, said electrode base adapted to receive at least one electrode pad;
   said headset body and said base adapted to orient an electrical stimulation surface of said pad towards the skin surface, during donning by the user;
   said elastic arrangement adapted such that, during said donning, said elastic arrangement radially urges said electrode base towards the skin surface such that said electrode pad makes physical and electrical contact with the skin surface;
   said elastic arrangement and said electrode base adapted such that for various degrees of tensioning of said elastic arrangement, a circumferential position of said electrode base, with respect to said frame, is fixed in a specific predetermined position;
   said circumferential headset body having a rear section adapted to fit around a rear portion of the head, at least one of said at least one electrode base being a rear electrode base disposed on said rear portion.

18. The headset of claim 17, said rear section being a rear mechanical element that is physically distinct from said circumferential headset body.

19. The headset of claim 18, said rear mechanical element spanning at most 40% of a circumference of said circumferential headset body.

20. The headset of claim 17, said circumferential headset body having a front section adapted to fit around a front portion of the head, said at least one of said at least one electrode base being a front electrode base disposed on said front portion.

21. The headset of claim 17, said frame including at least semi-rigid side components, bi-laterally disposed on said frame, and forming side portions of said circumference of said headset body.

22. The headset of claim 17, said frame including at least a first bi-lateral size adjustment mechanism adapted to fixedly adjust said circumference of said headset body.

23. The headset of claim 17, said headset body adapted to juxtapose a contact surface of an electrical device opposite or against the skin surface, said elastic arrangement adapted to radially urge said electrical device towards said skin surface such that a contact surface of said electrical device makes physical contact with said skin surface; said elastic arrangement adapted such that for various degrees of tensioning of said elastic arrangement, a circumferential position of said electrical device is fixed in a particular device position.

24. The headset of claim 23, said electrical device including a sensor adapted to sense a body parameter associated with the head of the user.

25. The headset of claim 17, said at least one electrode pad including:
   (a) a liquid-absorbent layer having a biocompatible, conductive contact surface, said contact surface adapted to be juxtaposed against the skin surface;
   (b) an electrically conductive layer having a broad first face juxtaposed against, or attached to, said liquid-absorbent layer, said conductive layer containing at least one electrically conductive material or element, said conductive layer adapted to transfer an electrical current from a broad second face, distal to said first face, to said liquid-absorbent layer, via said first face.

26. A headset for use in delivering electrical stimulation to a skin surface of a head of a user, the headset comprising:
(a) a circumferential headset body, said body having a monolithic frame adapted to circumferentially fit around the head of the user, said body housing an electric circuit adapted to be connected to a power source; said headset body including an elastic arrangement, disposed on at least a portion of a circumference of said headset body;
(b) at least one electrode pad, said pad including:
 (i) a liquid-absorbent layer having a biocompatible contact surface, said contact surface adapted to be juxtaposed against the skin surface;
 (ii) an electrode backing, attached to said liquid-absorbent layer, said backing containing at least one electrically conductive material or element, said conductive material or element being electrically connected with said liquid-absorbent layer, when said liquid-absorbent layer is filled with liquid;
(c) at least one electrode base, mechanically and at least semi-rigidly connected to said headset body, and electrically associated with said electric circuit, said electrode base adapted to receive at least one electrode pad;
said headset body and said base adapted to orient an electrical stimulation surface of said pad towards the skin surface, during donning by the user;
said elastic arrangement adapted such that, during said donning, said elastic arrangement radially urges said electrode base towards the skin surface such that said electrode pad makes physical and electrical contact with the skin surface;
said elastic arrangement and said electrode base adapted such that for various degrees of tensioning of said elastic arrangement, a circumferential position of said electrode base, with respect to said frame, is fixed in a specific predetermined position;
said biocompatible contact surface having:
(i) a long dimension ($D_L$) having a maximum length of 20 mm to 55 mm;
(ii) a narrow dimension ($D_N$) having a maximum length of 10 mm to 25 mm;
wherein a first side of a perimeter of said biocompatible contact surface has a generally concave contour having a concavity defined by first and second boundary points disposed at opposite ends of said concavity,
wherein:

$A/L \geq 0.5$ mm

A being an area bounded by said line and said concavity;
L being a length of a line between said boundary points;
said length (L) being at least 10 mm;
wherein a line disposed between a first point on said concave contour and a second point on said perimeter, on a side opposite said concave contour, and aligned in perpendicular fashion with respect to said contour at said first point, has a length H, and wherein, over an entirety of said concave contour, $H_{max}/H_{min} \leq 2.5$, $H_{max}$ being a maximum value of H over said entirety; and $H_{min}$ being a minimum value of H over said entirety.

27. The headset of claim 26, said circumferential headset body having a front section adapted to fit around a front portion of the head, said at least one of said at least one electrode base being a front electrode base disposed on said front portion.

28. The headset of claim 26, said frame including at least semi-rigid side components, bi-laterally disposed on said frame, and forming side portions of said circumference of said headset body.

29. The headset of claim 26, said frame including at least a first bi-lateral size adjustment mechanism adapted to fixedly adjust said circumference of said headset body.

30. The headset of claim 26, said headset body adapted to juxtapose a contact surface of an electrical device opposite or against the skin surface, said elastic arrangement adapted to radially urge said electrical device towards said skin surface such that a contact surface of said electrical device makes physical contact with said skin surface; said elastic arrangement adapted such that for various degrees of tensioning of said elastic arrangement, a circumferential position of said electrical device is fixed in a particular device position.

31. The headset of claim 30, said electrical device including a sensor adapted to sense a body parameter associated with the head of the user.

32. The headset of claim 26, said at least one electrode pad including:
(a) a liquid-absorbent layer having a biocompatible, conductive contact surface, said contact surface adapted to be juxtaposed against the skin surface;
(b) an electrically conductive layer having a broad first face juxtaposed against, or attached to, said liquid-absorbent layer, said conductive layer containing at least one electrically conductive material or element, said conductive layer adapted to transfer an electrical current from a broad second face, distal to said first face, to said liquid-absorbent layer, via said first face.

33. A headset for use in delivering electrical stimulation to a skin surface of a head of a user, the headset comprising:
(a) a circumferential headset body, said body having a monolithic frame adapted to circumferentially fit around the head of the user, said body housing an electric circuit adapted to be connected to a power source; said headset body including an elastic arrangement, disposed on at least a portion of a circumference of said headset body;
(b) at least one electrode base, mechanically and at least semi-rigidly connected to said headset body, and electrically associated with said electric circuit, said electrode base adapted to receive at least one electrode pad;
said headset body and said base adapted to orient an electrical stimulation surface of said pad towards the skin surface, during donning by the user;
said elastic arrangement adapted such that, during said donning, said elastic arrangement radially urges said electrode base towards the skin surface such that said electrode pad makes physical and electrical contact with the skin surface;
said elastic arrangement and said electrode base adapted such that for various degrees of tensioning of said elastic arrangement, a circumferential position of said electrode base, with respect to said frame, is fixed in a specific predetermined position;
said at least one electrode pad including:
(a) a liquid-absorbent layer having a biocompatible, conductive contact surface, said contact surface adapted to be juxtaposed against the skin surface;

(b) an electrically conductive layer having a broad first face juxtaposed against, or attached to, said liquid-absorbent layer, said conductive layer containing at least one electrically conductive material or element, said conductive layer adapted to transfer an electrical current from a broad second face, distal to said first face, to said liquid-absorbent layer, via said first face;

said electrically conductive layer having, on said second face, a layer of electrically conductive paint, preferably disposed in a mesh pattern.

34. The headset of claim 33, said liquid-absorbent layer and said electrically conductive layer having said layer of electrically conductive paint forming an integral structure.

35. The headset of claim 33, said circumferential headset body having a front section adapted to fit around a front portion of the head, said at least one of said at least one electrode base being a front electrode base disposed on said front portion.

36. The headset of claim 33, said frame including at least semi-rigid side components, bi-laterally disposed on said frame, and forming side portions of said circumference of said headset body.

37. The headset of claim 33, said frame including at least a first bi-lateral size adjustment mechanism adapted to fixedly adjust said circumference of said headset body.

38. The headset of claim 33, said headset body adapted to juxtapose a contact surface of an electrical device opposite or against the skin surface, said elastic arrangement adapted to radially urge said electrical device towards said skin surface such that a contact surface of said electrical device makes physical contact with said skin surface; said elastic arrangement adapted such that for various degrees of tensioning of said elastic arrangement, a circumferential position of said electrical device is fixed in a particular device position.

39. The headset of claim 38, said electrical device including a sensor adapted to sense a body parameter associated with the head of the user.

40. A headset for use in delivering electrical stimulation to a skin surface of a head of a user, the headset comprising:
(a) a circumferential headset body, said body having a monolithic frame adapted to circumferentially fit around the head of the user, said body housing an electric circuit adapted to be connected to a power source; said headset body including an elastic arrangement, disposed on at least a portion of a circumference of said headset body;
(b) at least one electrode base, mechanically and at least semi-rigidly connected to said headset body, and electrically associated with said electric circuit, said electrode base adapted to receive at least one electrode pad; said headset body and said base adapted to orient an electrical stimulation surface of said pad towards the skin surface, during donning by the user;

said elastic arrangement adapted such that, during said donning, said elastic arrangement radially urges said electrode base towards the skin surface such that said electrode pad makes physical and electrical contact with the skin surface;

said elastic arrangement and said electrode base adapted such that for various degrees of tensioning of said elastic arrangement, a circumferential position of said electrode base, with respect to said frame, is fixed in a specific predetermined position;

said at least one electrode pad including:
(a) a liquid-absorbent layer having a biocompatible, conductive contact surface, said contact surface adapted to be juxtaposed against the skin surface;
(b) an electrically conductive layer having a broad first face juxtaposed against, or attached to, said liquid-absorbent layer, said conductive layer containing at least one electrically conductive material or element, said conductive layer adapted to transfer an electrical current from a broad second face, distal to said first face, to said liquid-absorbent layer, via said first face;

said electrically conductive layer containing a carbon foil.

41. The headset of claim 40, said carbon foil having a resistivity within a range of 1-180 ohm/square or 30-100 ohm/square.

42. The headset of claim 40, said circumferential headset body having a front section adapted to fit around a front portion of the head, said at least one of said at least one electrode base being a front electrode base disposed on said front portion.

43. The headset of claim 40, said frame including at least semi-rigid side components, bi-laterally disposed on said frame, and forming side portions of said circumference of said headset body.

44. The headset of claim 40, said frame including at least a first bi-lateral size adjustment mechanism adapted to fixedly adjust said circumference of said headset body.

45. The headset of claim 40, said headset body adapted to juxtapose a contact surface of an electrical device opposite or against the skin surface, said elastic arrangement adapted to radially urge said electrical device towards said skin surface such that a contact surface of said electrical device makes physical contact with said skin surface; said elastic arrangement adapted such that for various degrees of tensioning of said elastic arrangement, a circumferential position of said electrical device is fixed in a particular device position.

46. The headset of claim 45, said electrical device including a sensor adapted to sense a body parameter associated with the head of the user.

* * * * *